(12) United States Patent
Moss et al.

(10) Patent No.: US 9,078,665 B2
(45) Date of Patent: Jul. 14, 2015

(54) MULTIPLE TREATMENT ZONE ABLATION PROBE

(71) Applicant: AngioDynamics, Inc., Latham, NY (US)

(72) Inventors: Kevin Moss, Tracy, CA (US); Robert Pearson, San Jose, CA (US)

(73) Assignee: AngioDynamics, Inc., Latham, NY (US)

( * ) Notice: Subject to any disclaimer, the term of this patent is extended or adjusted under 35 U.S.C. 154(b) by 246 days.

(21) Appl. No.: 13/630,135

(22) Filed: Sep. 28, 2012

(65) Prior Publication Data

US 2013/0090646 A1   Apr. 11, 2013

Related U.S. Application Data

(60) Provisional application No. 61/540,190, filed on Sep. 28, 2011.

(51) Int. Cl.
| | |
|---|---|
| *A61B 18/18* | (2006.01) |
| *A61B 18/04* | (2006.01) |
| *A61B 18/14* | (2006.01) |
| *A61B 18/00* | (2006.01) |
| *A61B 19/00* | (2006.01) |

(52) U.S. Cl.
CPC ............ *A61B 18/1487* (2013.01); *A61B 18/18* (2013.01); *A61B 18/1815* (2013.01); *A61B 2018/00083* (2013.01); *A61B 2018/00273* (2013.01); *A61B 2018/00529* (2013.01); *A61B 2018/00577* (2013.01); *A61B 2018/00589* (2013.01); *A61B 2018/00613* (2013.01); *A61B 2018/1467* (2013.01); *A61B 2018/1475* (2013.01); *A61B 2019/306* (2013.01)

(58) Field of Classification Search
USPC ..................................... 606/27, 41
See application file for complete search history.

(56) References Cited

U.S. PATENT DOCUMENTS

2010/0204638 A1*   8/2010   Hobbs et al. .................... 604/20

* cited by examiner

*Primary Examiner* — Nicole F Lavert
(74) *Attorney, Agent, or Firm* — Peter J. Flora

(57) ABSTRACT

An energy delivery probe and method of using the energy delivery probe to treat a patient is provided herein. The energy delivery probe has at least one probe body having a longitudinal axis and at least a first trocar and a second trocar. Each trocar comprises at least two electrodes that are electrically insulated from each other, and each electrode is independently selectively activatable. An insulative sleeve is positioned in a coaxially surrounding relationship to each of the first trocar and the second trocar. The probe also has a switching means for independently activating at least one electrode. The method involves independently and selectively activating the first and second electrodes to form an ablation zone, then repeating the ablation by delivering energy to a second set of electrodes, producing one or more overlapping ablation zone, and eliminating the need to reposition the ablation probes.

11 Claims, 15 Drawing Sheets

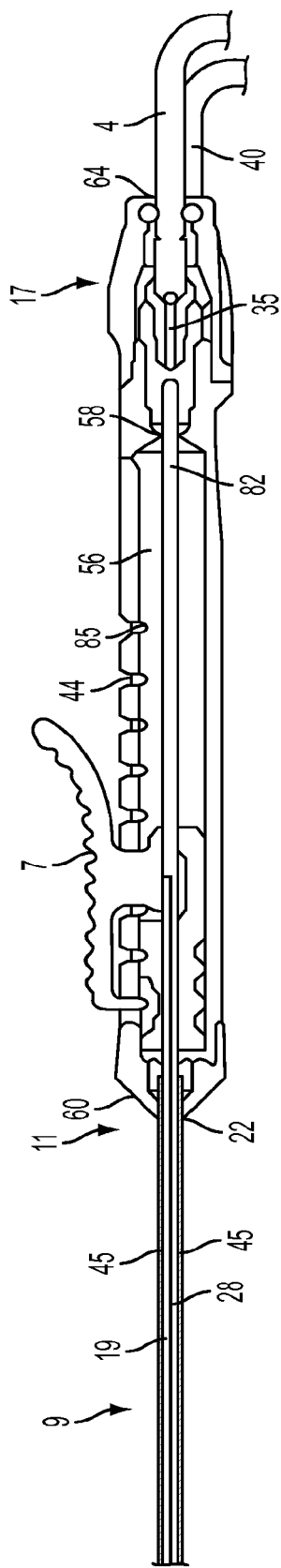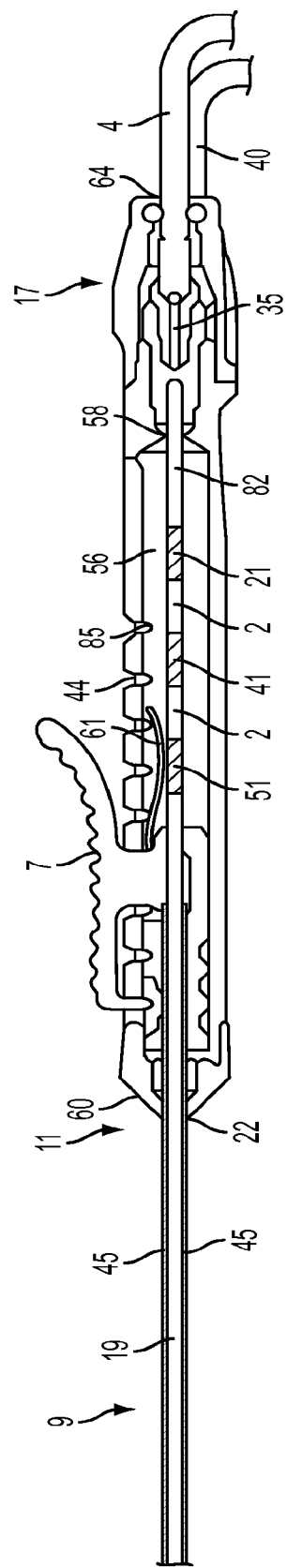
FIG. 5A
FIG. 5B

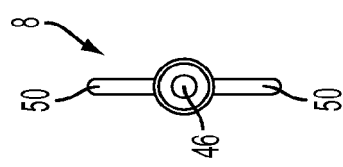
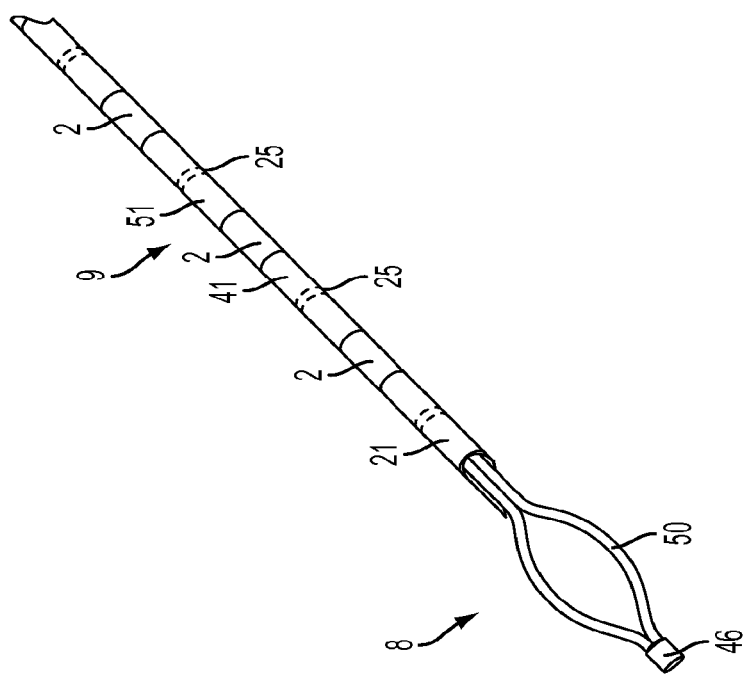
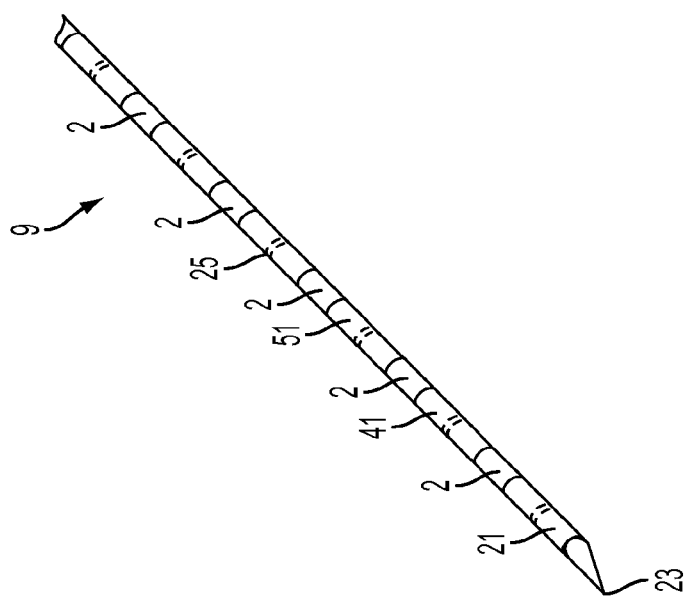

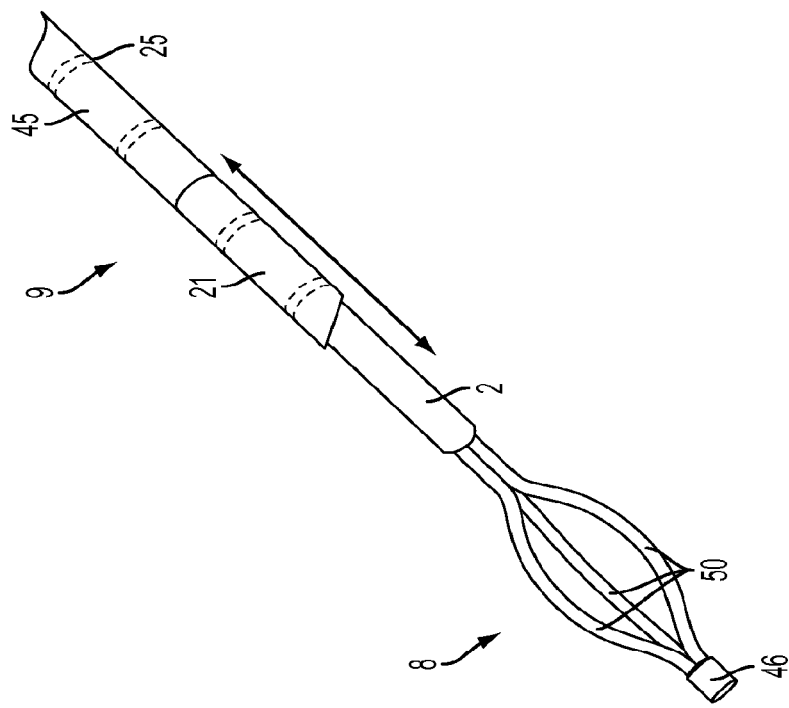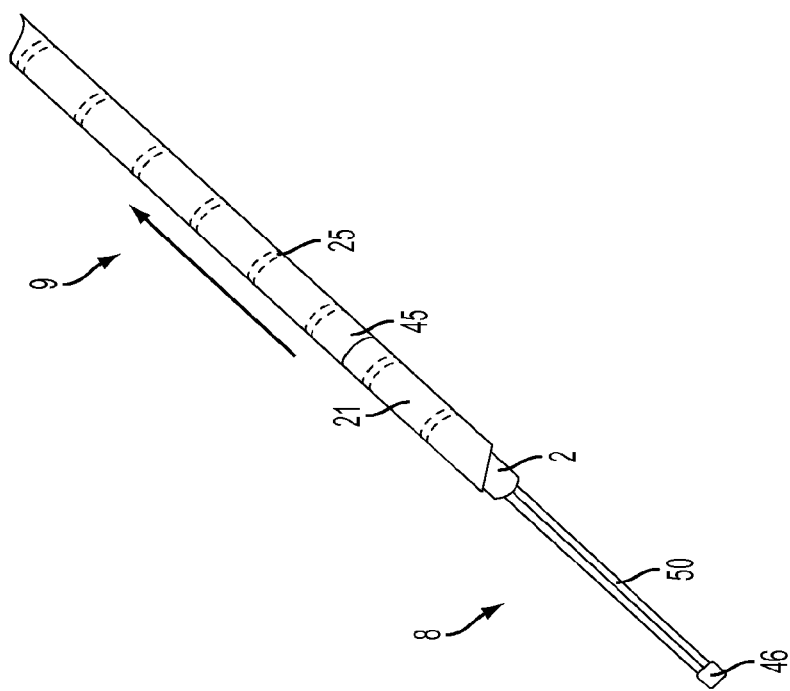

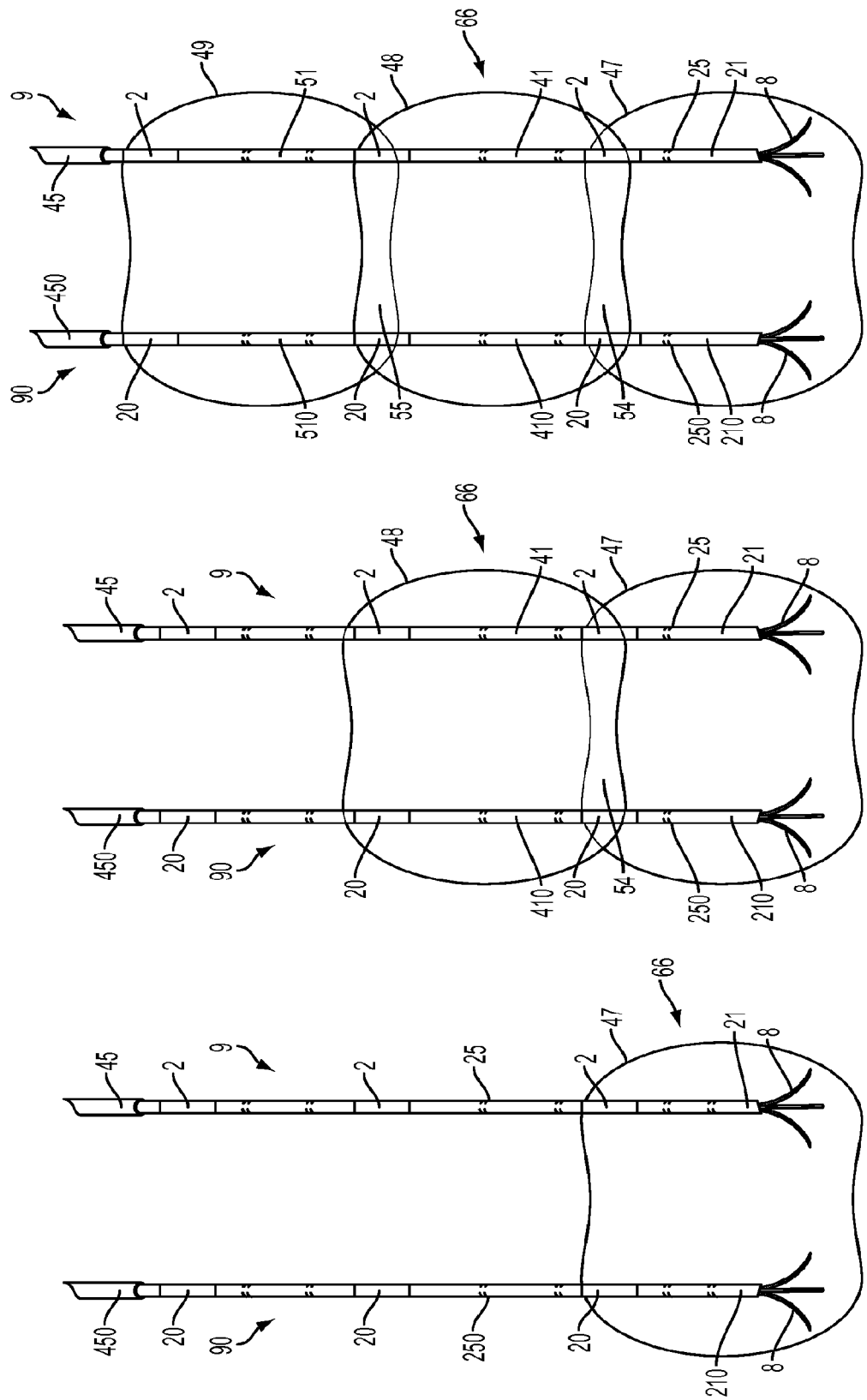

MULTIPLE TREATMENT ZONE ABLATION PROBE

TECHNICAL FIELD

The present invention relates to an energy delivery probe and method of treatment using the energy delivery probe.

BACKGROUND OF THE INVENTION

Irreversible electroporation (IRE) is a non-thermal, minimally invasive surgical technique to ablate undesirable tissue, for example, tumor tissue. The technique is easy to apply, can be monitored and controlled, is not affected by local blood flow, and does not require the use of adjuvant drugs. The minimally invasive procedure involves placing needle-like electrodes into or around a targeted tissue area to deliver a series of short and intense electric pulses that induce structural changes in the cell membranes that promote cell death.

Another technique for ablating a desired target tissue is radiofrequency ablation (RFA). This procedure involves using an imaging guidance system such as ultrasound (US), computed tomography (CT), or magnetic resonance (MR). During this procedure, a physician places a probe directly into a target tissue area, such as a tumor. Using an energy source, a physician or other practitioner can then deliver a carefully-controlled amount of energy to flow through the electrodes into the tissue which causes the tissue to heat up. The heating is sustained for a predetermined length of time, usually just a few minutes, which kills and destroys the target tissue. RFA procedures can be percutaneously or laparoscopically performed.

Among the problems associated with current IRE procedures is that with current single IRE probe electrode designs, it is common practice for physicians to perform multiple overlapping or stacked ablations. In between each ablation, the physician has to reposition the probes. During this repositioning or pull-back process, however, it is sometimes difficult for physicians to keep all of the probes parallel for ablations that are performed after the first ablation. In addition, it is difficult to know exactly where the first ablation ends and how much overlap there is between successive ablations, which can increase the chances of missing portions of a target tumor tissue between the ablations or may result in unusual or unpredictable ablation shapes.

Another problem that sometimes occurs with current single IRE or RF ablation probes is probe migration. This occurs when an ablation probe moves slightly from the original position were the probe was inserted, either during the placement of additional probes or during an actual ablation procedure. When this occurs, an undertreated area of target tissue can potentially be left behind, or unintended target tissue can be ablated, or alternatively, a vital organ or structure can be damaged by the tip of a needle.

There exists a need in the art for an improved ablation probe and method of using such a probe for improved IRE and RF ablations that will allow a practitioner to more easily predict and control the location and size of IRE and RF ablations and provide the ability to easily maintain the electrodes in a stationary position within tissue before, during, and after an ablation. An electrode probe and method has not yet been proposed that would solve the problems described above, thereby avoiding many of the negative side effects of the current devices described above.

It is a purpose of the invention described herein to provide a dual probe device in which each probe has at least two electrode regions that can be switched between an active energy delivery state and a non-active non-energy delivery state, depending in the desired ablation zone(s), during either IRE or RF ablations.

It is also a purpose of this invention to provide various anchoring means at the distal tip of the ablation probe described herein in order to anchor at least portion of an active portion of the probe(s) relative to a patient's tissue throughout an ablation procedure.

It is also a purpose of this invention to provide an ablation probe that incorporates a means of adjusting the active portion of the electrode axially along the trocar, or the ablation probe may incorporate a plurality of fixed active portions along the trocar in order to allow the user to create multiple ablations along a specific controlled path through a lesion without repositioning the ablation device.

Various other objectives and advantages of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention can be found in the Detailed Description of the Invention.

SUMMARY

A method of treating a patient is presented herein. The method involves identifying a target tissue, providing at least one energy delivery probe having a longitudinal axis, at least a first trocar and a second trocar. In one embodiment, each of the trocars has a proximal portion and a distal portion can optionally have at least one lumen extending along the longitudinal axis. The distal portions of each of the trocars are capable of piercing tissue. Each of the trocars has at least two electrodes that are electrically insulated from each other. Each electrode is independently selectively activatable. The ablation probe also has an insulative sleeve that is positioned in a coaxially surrounding relationship to at least a portion of each of the first trocar and the second trocar and a switching means for independently activating at least one electrode. The method further involves inserting the probe into or near the target tissue, activating at least a first electrode on the first trocar and a first electrode on the second trocar, and delivering energy to the target tissue to ablate the tissue, thereby forming at least one ablation zone. The ablation method can be repeated between various sets of electrodes between the trocars to produce multiple overlapping ablation zones.

Also described herein is a variation of the ablation method described above. The method involves identifying a target tissue, providing at least one energy delivery probe, as described above, which energy delivery probe further includes at least one anchoring means that is capable of being deployed from the distal end of the probe, inserting the probe into or near the target tissue, deploying the at least one anchoring means, activating at least a first electrode on the first trocar and a first electrode on the second trocar, and delivering energy to the target tissue to ablate the tissue, thereby forming at least one ablation zone. The ablation procedure can be repeated multiple times, thereby causing multiple overlapping ablation zones.

A probe device is also presented herein that has a longitudinal axis and at least a first trocar and a second trocar. Each of the trocars comprises a proximal portion and a distal portion and a lumen extending along the longitudinal axis. The distal portions of the trocars are capable of piercing tissue. Each trocar has at least two electrodes that are electrically insulated and separated from each other, and each electrode is independently selectively activatable.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 5A illustrates an enlarged longitudinal sectional view of one embodiment of the handle of the energy delivery probe.

FIG. 5B illustrates an enlarged longitudinal sectional view of another embodiment of the handle of the energy delivery probe.

FIG. 6A illustrates an enlarged perspective view of a portion of the distal end of the trocar with an anchoring means retracted inside of the energy delivery probe.

FIG. 6B illustrates an enlarged perspective view of a portion of the distal end of the trocar with an anchoring means deployed from the distal end of the energy delivery probe.

FIG. 6C illustrates an end view of the distal end of the trocar of FIGS. 6A and 6B.

FIG. 7A illustrates an enlarged perspective view of a portion of the distal end of the probe with an anchoring means extending from the distal end of the energy delivery probe.

FIG. 7B illustrates an enlarged perspective view of a portion of the distal end of the probe with another embodiment of an anchoring means in a deployed state.

FIG. 7C illustrates an end view of the anchoring means of FIGS. 7A and 7B.

FIG. 15A illustrates an exemplary single ablation zone that is produced after an anchoring means is deployed and a first ablation is completed.

FIG. 15B illustrates exemplary overlapping first and second ablation zones that are produced after an anchoring means is deployed and a first and second ablation are produced.

FIG. 15C illustrates exemplary overlapping first, second, and third ablation zones that are produced after an anchoring means is deployed and first, second, and third ablations are completed.

DETAILED DESCRIPTION OF THE INVENTION

Figure 1:
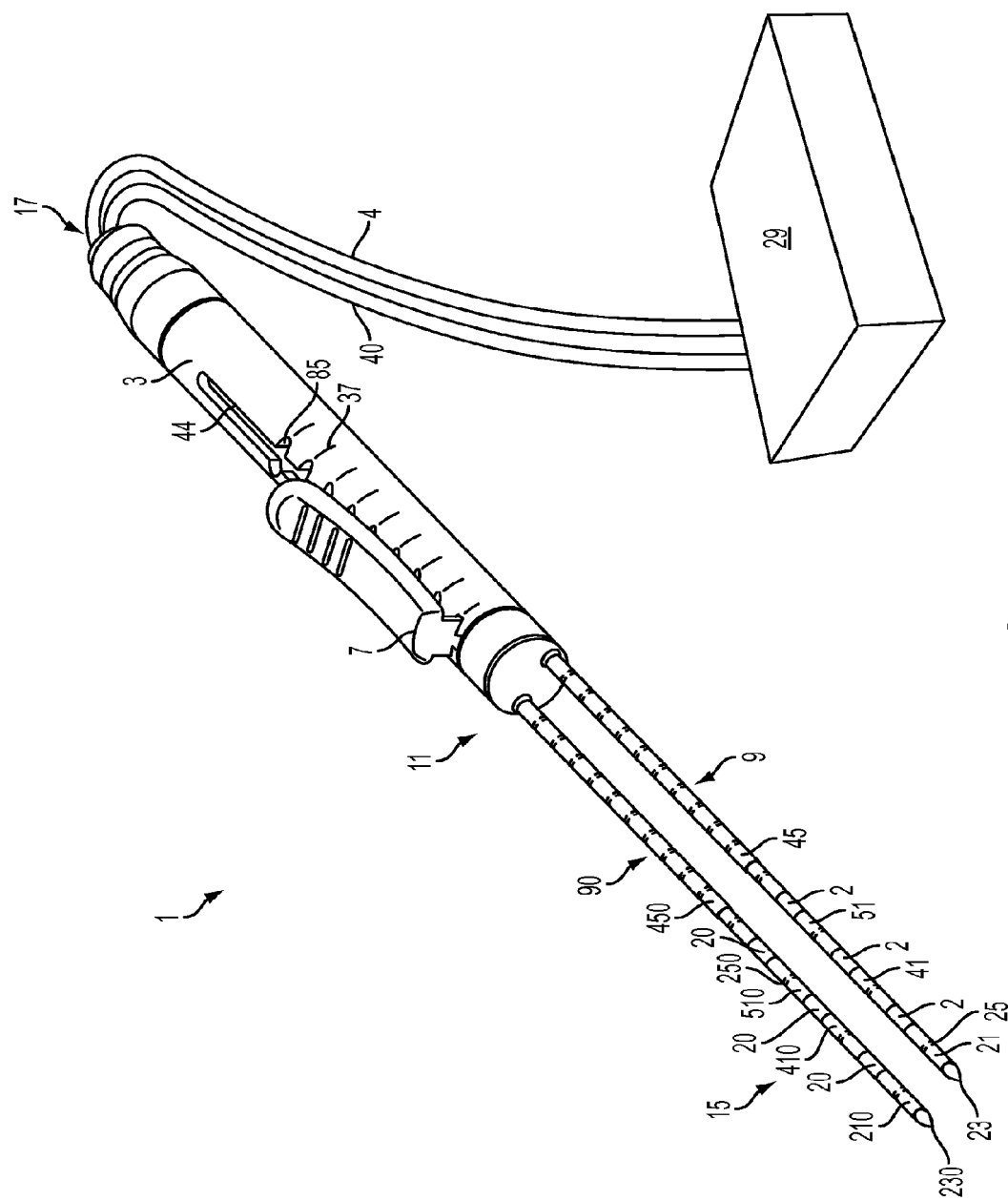
FIG. 1 illustrates a perspective view of a first embodiment of an energy delivery probe device.

The present invention can be understood more readily by reference to the following detailed description and the examples included therein and to the Figures and their previous and following description. The drawings, which are not necessarily to scale, depict selected embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Ranges can be expressed herein as from "about" to one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, the words "proximal" and "distal" refer to directions away from and closer to, respectively, the insertion tip of the probe in the probe. The terminology includes the words above specifically mentioned, derivatives thereof, and words of similar import.

Other than in the operating examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can be varied as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values can be used.

"Formed from" and "formed of" denote open claim language. As such, it is intended that a member "formed from" or "formed of" a list of recited components and/or materials be a member comprising at least these recited components and/or materials, and can further include other non-recited components and/or materials.

Examples provided herein, including those following "such as" and "e.g." are considered as illustrative only of various aspects and features of the present disclosure and embodiments thereof, without limiting the scope of any of the referenced terms or phrases either within the context or outside the context of such descriptions. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Some of these examples are themselves sufficient for practice singly (including their equivalents, alternatives, and modifications) without being combined with any other features, as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner.

As used herein, "substantially", "generally", and other words of degree are relative modifiers intended to indicate permissible variation from the characteristic so modified. It is not intended to be limited to the absolute value or characteristic which it modifies, but rather possessing more of the physical or functional characteristic than its opposite, and preferably, approaching or approximating such a physical or functional characteristic. "Optional" or "optionally" means that the subsequently described element, event or circumstance can or cannot occur, and that the description includes instances where said element, event or circumstance occurs and instances where it does not. The term "ablation" is used herein to refer to either irreversible electroporation (IRE) ablations or radiofrequency ablation (RFA) ablations or both. "IRE ablation device" is used herein to refer to any of the devices described herein that can be used for IRE ablations, "RFA devices" can be used herein to refer to any of the devices described herein that can be used for RF ablations. All dimensions herein are exemplary, and one of ordinary skill in the art will recognize that other dimensions possible.

Referring now in detail to the drawings, in which like reference numerals indicate like parts or elements throughout the several views, in various embodiments, presented herein is an exemplary ablation device that can be used for RF or IRE ablations.

FIG. 1 illustrates one exemplary embodiment of an energy delivery probe 1 for use in treating a patient. The probe can be an RF ablation probe or an IRE ablation probe. The probe 1 has a proximal end 17, a distal end 15 and a longitudinal axis. At least a portion of the proximal end 17 of the probe 1 can be configured to be positioned outside of a human body. At least a portion of the distal end 15 of the probe 1 can be configured to be inserted into at least a portion of a human body, such as, but not limited to, a target tissue.

The probe 1 further comprises an elongate probe body. The elongate body can comprise a trocar 9 having a proximal end, a distal end, and at least one selectively activatable electrode 21, 41, 51. The probe body can be substantially fixed in relation to the trocar 9.

The probe body comprises a handle 3 that can be positioned at the proximal end 17 of the probe 1. The proximal end 17 of the probe and the proximal end of the handle 3 are interchangeably referred to herein. The handle 3 has a distal end 11, an outer surface, and an interior cavity 58. The probe 1 can be operatively coupled at the proximal end 17 of the handle 3 to an energy source 29 by at least one cable 4. A portion of the cable 4 is positioned within at least a portion of the handle 3, such that the at least one cable 4 is adjacent to the proximal end of the probe 1 and extends proximally from the proximal end 17 of the handle 3.

The power source can be, but is not limited to, an RF source, an electrical energy source, or microwave source. In one aspect, the energy source 29 can be a generator. The generator is configured for supplying energy to the probe 1 in a controlled manner. The energy delivery source can be capable of delivering energy that such as, but not limited to, radiofrequency (RF) energy and electrical energy. Such generators can include, but are not limited to, a RITA® 1500X RF generator (AngioDynamics, Inc., Latham, N.Y.) or a NanoKnife® generator (AngioDynamics, Inc., Latham, N.Y.).

The handle 3 has at least one moveable slide member 7 comprising at least one slot 44. The slot 44 is defined within the outer surface of the handle 3 and extends along the longitudinal axis of the probe. The slot 44 further comprises a plurality of grooves 85 that are positioned at a substantially right angle to the longitudinal axis of the slot 44. The handle 3 can be made of any suitable material, such as, but not limited to, ABS plastic or other similar plastics, such as PEEK.

The at least one slide member 7 is slidably disposed an the handle 3. In one aspect, the slide member 7 can be a finger-actuatable slide member 7. At least a portion of the slide member 7 is slidably received within slot 44. The slide member 7 can be manually and axially slidably actuated in a proximal or a distal direction along the longitudinal axis of the probe 1 such that at least a portion of the slide member 7 can be slidably received and locked into place in a single groove 85. Each groove 85 corresponds with an index marking 37. Each marking 37 corresponds with an electrode deployment length and can be used to indicate to a user the required depth of electrode deployment from tracer 9 needed for 2, 3, and 4 cm diameter tissue ablations, for example. At least a portion of the slide member 7 can be operatively coupled to a portion of at least one insulative sleeve 45, described below.

The tracer 9 has a proximal end, at least a portion of which can be positioned within the cavity of and operatively coupled the handle 3. The tracer 9 has a distal end 15. The distal end 15 of the tracer 9 and the distal end of the probe 1 are interchangeably used herein. The at least one tracer 9 and the handle 3 extend along the longitudinal axis of the probe 1. In one exemplary embodiment, the trocars 9, 90 can be spaced apart from about 1.5 cm to about 2.5 cm. The tracers can be of the same length or different lengths. Tracers of different lengths can enable a user to deploy the first trocar 9 to a first depth and a second tracer 90 to a second depth that is different from the first depth. In one exemplary embodiment, the tracers 9, 90 can be deployed to identical depths. The tracers 9, 90 extend distally from the handle 3 to a distal tip 23, 230. The distal tip 23, 230 can be sharp such that it is capable of piercing tissue. In one embodiment, at least a portion of the tracers 9, 90 can be rigid for IRE probes, but flexible or semi-flexible for RF probes. The rigid body and sharp tip 23, 230 of the tracer 9, 90 can be useful for penetrating target tissues, especially large, hard tumors.

The trocars 9 can have at least one lumen 19 (FIGS. 5A-5C) that extends along the longitudinal axis of the probe 1. If the probe 1 is an RF probe, the trocar 9 can be comprised of stainless steel or Inconel. If the probe 1 is an IRE probe, the tracer 9 can be comprised of a non-conductive material such as, but not limited to, polyimide or PEEK (polyether ether ketone). In one exemplary embodiment, the trocar 9 can be from about 13 gauge to about 15 gauge (1.828 mm to 1.449 mm) in size, depending on the desired treatment or a patient's anatomy. The tracer 9 can have a uniform diameter throughout its longitudinal length. The working length of the trocar 9 can be between about 10 cm and about 25 cm. The working length of the trocar is defined from a point just distal of the distal end of the handle 3 to the distal tip 23 of the trocar, depending on the size of the target tissue to be ablated and a patient's anatomy.

The trocars 9, 90 can comprise at least one index marker, such as, but not limited to at least one depth marking 25, 250 positioned along at least a portion of the outer surface of the trocar 9. The depth markers 25, 250 can be fixed in place and equi-distantly positioned from one another. In one exemplary embodiment, the markers 25, 250 can be spaced apart by about 1 cm. The depth markings 25 can be used to aid a practitioner in gauging the depth of deployment of the distal end of the ablation probe and for determining a desired ablation depth. Each of the tracers 9, 90 can have at least one active electrode region or activatable electrodes 21/210, 41/410, 51/510.

Additionally, an electrically insulative sleeve 45, 450 can be coaxially positioned in a surrounding relationship around at least a portion of at least one of the trocars 9, 90. The insulative sleeve 45, 450 can extend from the proximal end of the tracer 9 to within about 0.25 to about 0.5 inches from the distal tip 23, 230 of the electrode. In one embodiment, insulation sleeve 45, 450 can comprise a polyamide material. The insulation sleeve 45, 450 can be stationary, as illustrated in FIG. 1, thus causing the electrode or voltage delivery regions of each activatable electrode 21/210, 41/410, 51/510 to be fixed or stationary and non-adjustable. Each electrode is non-insulated and has an energy delivery surface. In this embodiment in which the insulative sleeve is stationary, the tracer can be flexible.

Figure 2:
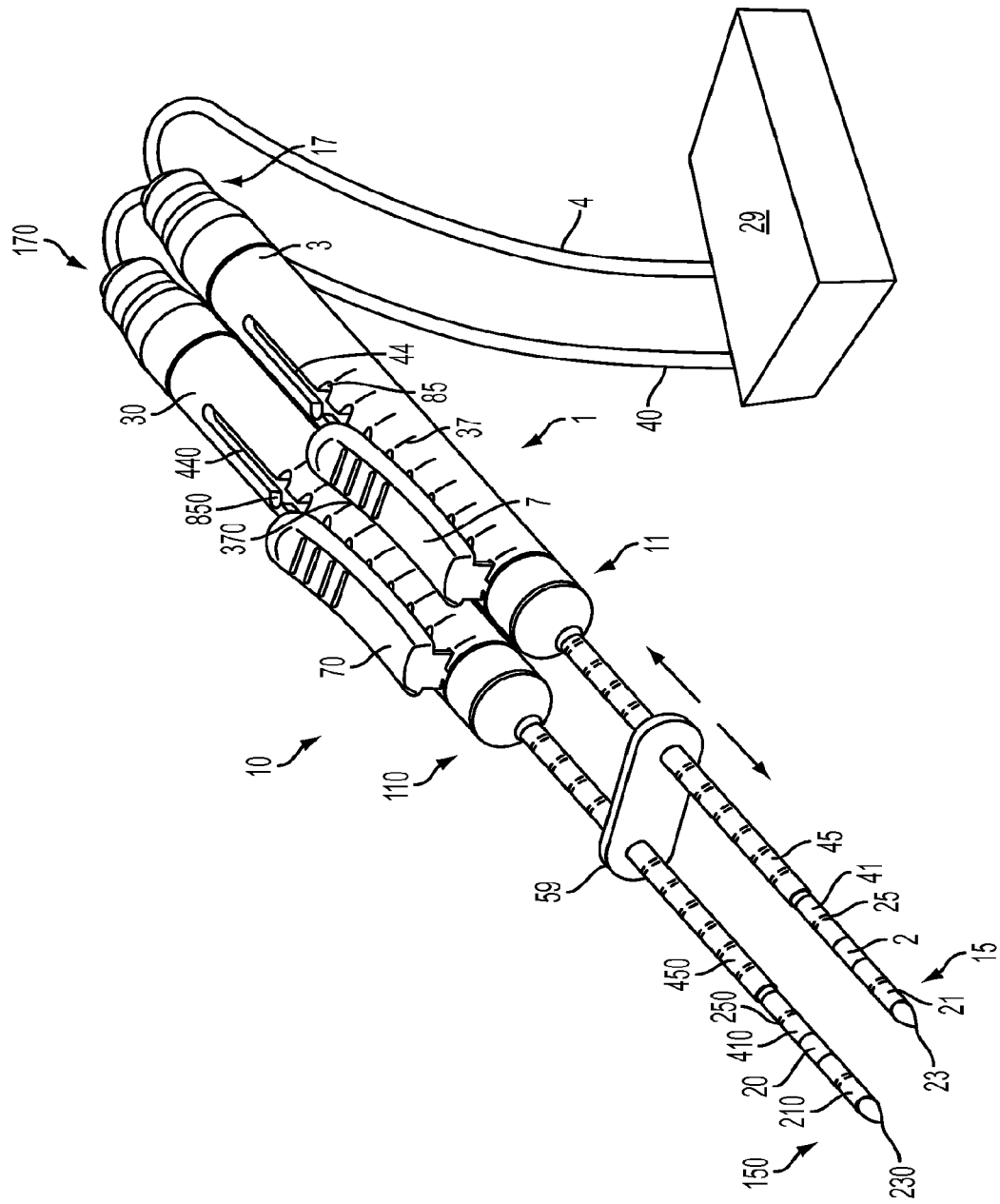
FIG. 2 illustrates a perspective view of a second embodiment of an energy delivery probe device.

In other exemplary embodiments, the insulative sleeve 45, 450 can be axially adjustable, as illustrated in FIGS. 2 and 7A, 7B. This allows a user to adjust or create an energy delivery surface of each of the electrodes, thereby adjusting the resulting ablation zones and the amount of overlap between ablation zones. The insulative sleeve can be mechanically coupled to the slide member or mechanical actuator on the handle member 3. In this embodiment, the trocar 9, 90 can be rigid or semi-rigid. The insulative sleeve 45, 450 can be proximally positioned and/or retracted to expose at least a portion of an energy delivery surface of at least one electrode 21/210, 41/410, 51/510. The exposed electrode(s) can provide at least one energy delivery surface along the surface of the trocar 9. One of ordinary skill in the art will recognize that the insulation sleeve 45, 450 can be initially positioned and/or adjusted along the length of the trocar 9, 90 to any desired position. The adjustable insulative sleeve 45 allows a practitioner to adjust the active electrode section(s) so that the ablation size may be altered, if desired. All or some portion of the insulation sleeve(s) 45 may be adjustably positioned so that the length of an energy delivery surface along the trocar 9 can be varied. As described below, the two or more electrodes 21/210, 41/410, 51/510 disposed along the length of the trocar can be electrically insulated from each other by at least one electrically insulating region 2, 20. The thickness of the insulative sleeve 45, 450 can vary, depending on whether the probe is an IRE probe or an RF probe. The insulation thickness may be varied because the operating voltage and currents of IRE and RF devices can be significantly different.

FIG. 2 illustrates a second embodiment of the probe 1. In this embodiment, the probe 1 can comprise two identical bipolar probes 1, 10, each having a trocar 9, 90, respectively. Alternatively, the probes can be monopolar. The probes 1, 10 can be positioned substantially parallel relative to one another. Each of the trocars 9, 90 can be spaced apart at a desired distance from each other such that the probes 1, 10, including the trocars 9, 90, remain parallel to one another at all times before, during, and after ablation. The trocars 9, 90 can be spaced at varying distances from each other depending on whether the probes 1, 10 are RF probes or IRE probes. In one exemplary embodiment, the tracers 9, 90 can be spaced about 1.5 cm-2.5 cm apart from each other. The bipolar probes 1, 10 described herein allow a physician to produce more controlled ablation zones, compared to current commercially available single RF or IRE ablation devices.

As described in U.S. patent application Ser. No. 13/028,431, filed Feb. 16, 2011, incorporated herein in its entirety ("Dual Bracketed Energy Delivery Probe and Method of Use"), a locking spacer 59 can be used to position and maintain the position of trocars 9, 90 such that they remain parallel to each other before, during, and after insertion and ablation treatment using the probes 1, 10. In one aspect, the locking spacer 59 can be a separate component that is capable of being axially slidably mounted onto at least a portion of the outer surface of the tracers 9, 90 for selectively positioning and retaining the pair of trocars 9, 90, and the probes 1, 10. The spacer 59 can be comprised of an ABS plastic material or a similar material. The spacer 59 can have any desired shape or size, such as, but not limited to, square or rectangular. The spacer 59 can have rounded edges. In one aspect, the spacer 59 can be transparent so that the markers 25 on the trocar 9 can remain visible to a practitioner.

Although not illustrated in detail, in one aspect, the spacer 59 can be between about 3 cm and 5 cm across the width of the trocars and between about 1 and 3 cm in thickness along the longitudinal length of the trocars. The spacer 59 can have a body with an outer surface and at least two bores: a first bore and a second bore. Each bore has an inner surface, and each bore is capable of receiving a portion of an outer surface of the first tracer 9 and the second tracer 90. The first and second bores can extend through the body of the spacer 59 such that they are in communication with the exterior of the spacer 59. The position of the bores within the spacer 59 can be adjusted to match a desired spacing between the tracers 9, 90. The bores can be capable of receiving at least a portion of the outer surface of each of tracers 9, 90. Each of the bores of the spacer 59 can be equal to or slightly smaller in diameter than the outer diameter of the insulative sleeves 45, 450 an the tracers 9, 90 in order to provide a sufficient interference fit between the outer surface of the insulative sleeve 45, 450 and the inner surface of the bores. Once the spacer 59 has been positioned along the trocars 9, 90, the interference fit between the outer surface of the insulative sleeve 45 and the inner surface of, the bores can prevent the spacer 59 from sliding out of a desired position during insertion and use. Although not illustrated, in one alternative embodiment, the spacer 59 can further comprise a locking mechanism.

The spacer 59 can be slideably moveable or adjustable in either a proximal or a distal direction along the longitudinal length of the trocars 9, 90. In one exemplary embodiment, the spacer 59 can be configured to be received into small grooves (not shown) that can be positioned along the longitudinal length of the outer surface of the insulative sleeves 45, 450. The spacer 59 can be provided in a kit that comprises at least the probes 1, 10, cables 4, 40, and optionally an energy source 29. In one aspect, more than one spacer 59 can be included in the kit. Different sized spacers having variously spaced bores could be included in the kit, depending on the desired ablation treatments.

As described above and illustrated in FIG. 3, each of the trocars 9, 90 can have two or more electrodes 21/210, 41/410, 51/510, each having a voltage delivery region and positioned along the outer surface of each of the trocars. Each of the electrodes can be adapted to receive electrical treatment energy from energy source 29. During use, each voltage delivery region of electrodes 21/210, 41/410, 51/510 can be activated from an inactive state to an active state to actively deliver energy to a target tissue. Energy can be delivered to the target tissue from energy source 29 through the voltage delivery regions or energy delivery surfaces of the electrodes to the target tissue. In one aspect, the energy delivery probe 1 described herein can be configured to operate as a bipolar probe device. Such bipolar probes are described in U.S. patent application Ser. No. 12/437,843, filed May 8, 2009 ("Electroporation Device and Method"), which application is incorporated herein by reference in its entirety.

The two more electrodes 21/210, 41/410, 51/510 disposed along the length of the trocar can be electrically insulated from each other by at least one electrically insulating region 2, 20. The at least one electrically insulating region(s) 2, 20 can separate the at least two activatable electrodes 21/210, 41/410, 51/510 in a manner sufficient to prevent electrical shorting as well as to prevent arcing between the activatable electrodes 21/210, 41/410, 51/510. In one exemplary embodiment, the electrically insulating regions 2, 20 can have a length of about 1 cm, while the electrodes 21/210, 41/410, 51/510 can have a length of about 2 cm. In one aspect, the insulating regions 2, 20 can be fixed and non-adjustable in dimensions.

Figure 3:
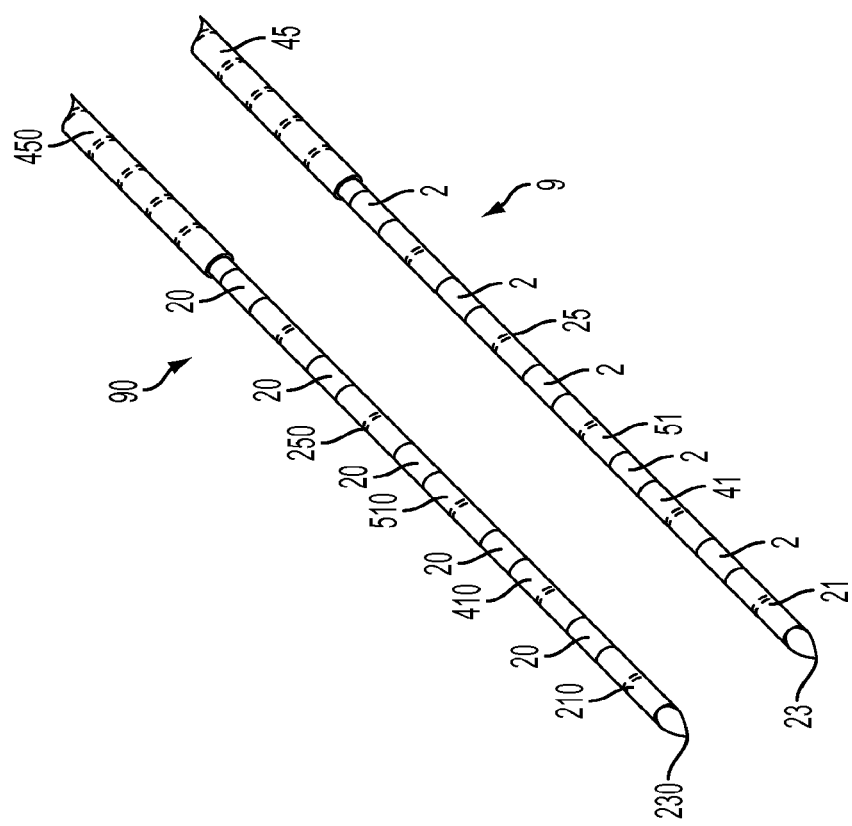
FIG. 3 illustrates an enlarged perspective view of the distal end of the probes of FIG. 2.

As illustrated in FIG. 3, the activatable electrode 21/210 can be positioned at a distal position on trocar 9, 90 such that when the trocars 9, 90 are inserted in a parallel position within target tissue, the activatable electrodes 21, 210 are positioned about 1.5 cm to 3 cm apart from each other. When positioned in a parallel position, together, the activatable electrodes 21, 210 form a first set of electrodes. A second set of electrodes, 41, 410 can be positioned on trocars 9, 90, respectively, proximally of the first set of electrodes. A third set of electrodes 51, 510 can be positioned along the trocar 9, 90 proximally of the first and second set of electrodes 41, 410. Although the device illustrated herein comprises three sets of electrodes, the ablation device can also comprise any suitable number of sets of electrodes, depending on the length of the trocar 9, 90, in order to effectively ablate a target tissue.

The collective size of the energy delivery surfaces of each of the first, second, and third sets of electrodes can be sufficient to create a volumetric ablation zone between any two of the electrodes of each set of electrodes when sufficient energy is delivered from the energy source to the ablation device.

Unless a portion of each of the electrodes is covered by insulation, then the entire length of each electrode is capable of functioning as an energy delivery surface which can deliver energy to a selected tissue mass. The length and size of each energy delivery surface can be variable. In one exemplary embodiment, the energy delivery surface of each electrode can be about 2 cm. In one exemplary embodiment, such as illustrated in FIGS. 1 through 3, the insulative sleeve 45, 450 can be stationary. In this embodiment, the active electrode regions are stationary and cannot be adjusted. In other exemplary embodiments, such as those illustrated in FIGS. 1A through 7C, the insulative sleeves 45, 450 can be adjustable, thereby allowing the length of the activatable electrodes 21/210, 41/410, 51/510 to be adjusted. The active working lengths or energy delivery surfaces of the electrodes can be adjustable by adjusting the position of the insulative sleeve covering the electrodes. Creation of different ablation geometries can be dependent on the length of energy ablation delivery surfaces, the number of electrodes, the size of the delivery surfaces of the electrodes, and the amount of power delivered to the electrodes.

Although not illustrated, in one aspect, any of the energy delivery devices described herein can optionally include at least one cooling mechanism. Such cooling mechanism can comprise the infusion of one or more liquids through the lumen 19 of the trocar 9. The trocar lumen 19 may be coupled to an infusion medium source and deliver an infusion medium to the selected tissue site. A cooling element can be coupled to at least one of the electrodes. The cooling element can be a structure positioned in at least one of the electrodes and can include at least one channel configured to receive a cooling medium. The cooling medium can be recirculated through the channel. RF probes described herein can also optionally include temperature feedback circuitry.

Figure 4A:
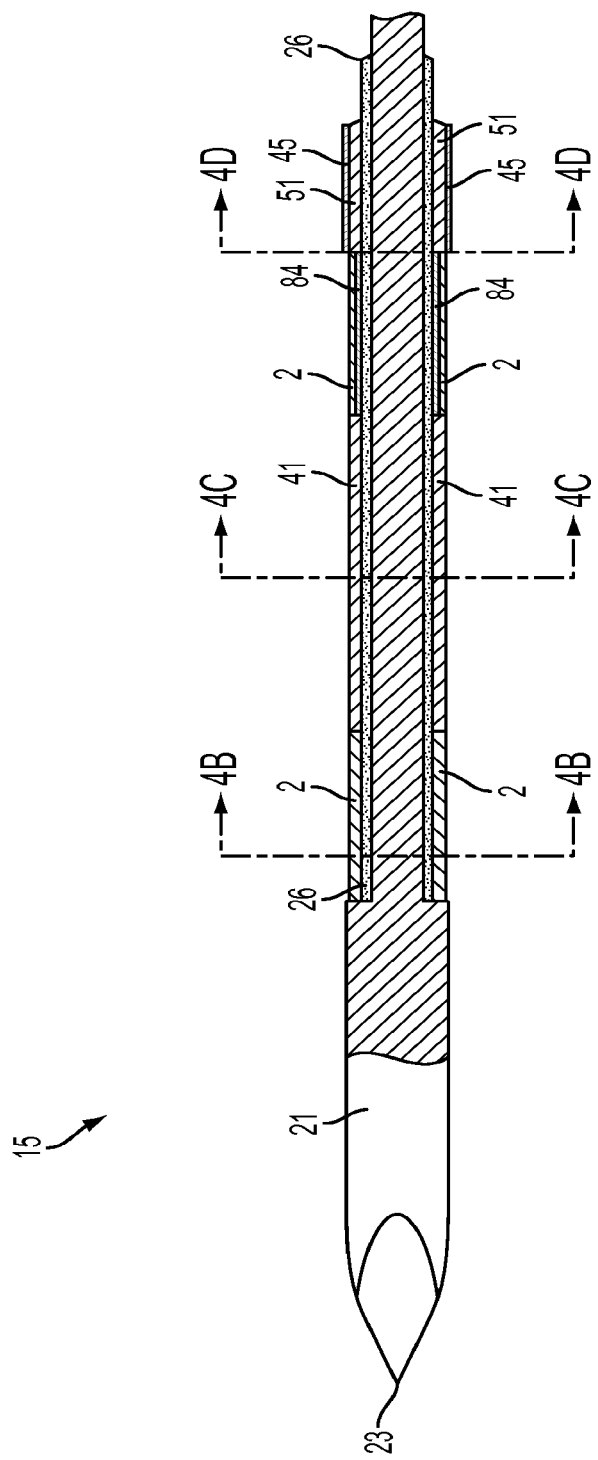
FIG. 4A illustrates a longitudinal cross-sectional view of the distal end of one of the probes of the energy delivery device of FIG. 1.
Figure 4D:
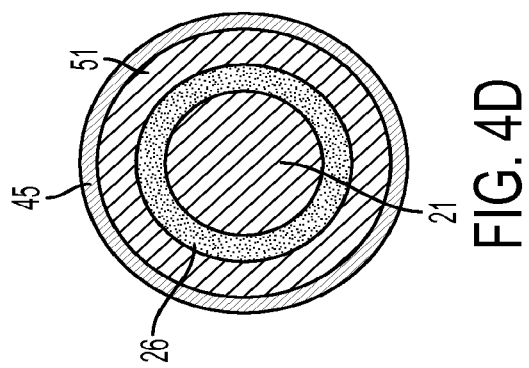
FIG. 4D illustrates a cross-sectional view along lines D-D of the energy delivery probe.
Figure 4C:
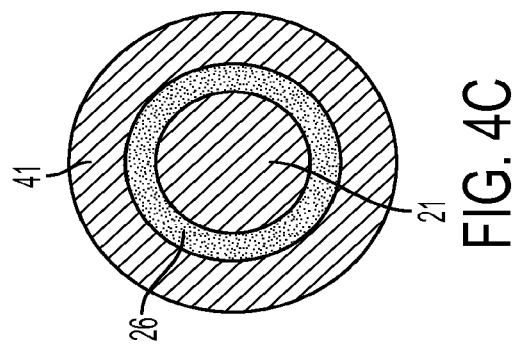
FIG. 4C illustrates a cross-sectional view along lines C-C of the energy delivery probe.
Figure 4B:
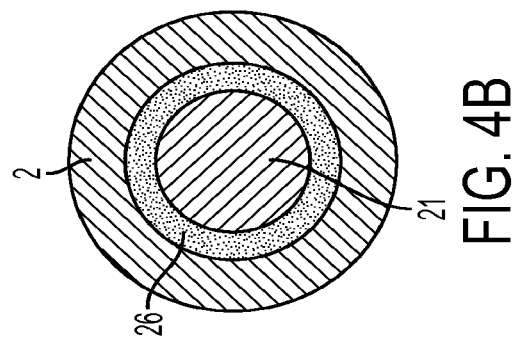
FIG. 4B illustrates a cross-sectional view along lines B-B of the energy delivery probe.

FIG. 4A is a longitudinal sectional view of the distal end of the trocar 9, 90. FIGS. 4B through 4E illustrate various cross-sectional views of the distal end of the trocar 9, 90. The activatable electrodes 21/210, 41/410 or voltage delivery members can be tubular structures coaxially disposed about electrically insulating member 26, having an inner diameter equal to or greater than the outer diameter of electrically insulating member 26. Activatable electrode 21 can be placed in a distally adjacent position to the insulating region 2. Activatable electrode 21 can include a distal portion for voltage delivery, and a proximal portion that can be electrically conducting for electrically coupling the activatable electrode 21 to an energy source 29. The electrode 21 can have a uniform outer diameter along its length. The uniform outer diameter can be substantially the same as the outermost diameters shown in FIGS. 4B-4D, so that the body portion of probe 10 can be substantially uniform in diameter along its length. The orientation and width of the electrically conducting (i.e., active electrode portions) and alternating insulating portions can be arranged so as to provide the probe with a substantially similar and constant diameter throughout its length. Alternatively, the insulating regions 2, 20 can be adjusted in width to provide a variable diameter trocar 9, 90, depending on the diameters of the activatable electrodes 21/210, 41/410 and the insulating regions 2, 20 in relation to each other. The thickness of electrically insulating regions 2, 20 can, in certain embodiments, be about 0.05 inches or less, and in additional embodiments can be 0.03 inches or less. Electrically insulating regions 2, 20 can include a plurality of indexing methods, including depth markings that can be detectable to an operator.

Insulative regions 2, 20 can be comprised of electrically non-conductive materials. Suitable electrically non-conductive materials can have a dielectric strength of 10 MV/m or greater, such as 15 MV/m or greater, or 20 MV/m or greater. Electrically non-conductive materials for insulating regions 2, 20 can include thermosets and thermoplastics, such as polyether ether ketone, polyphenylene sulfide, fluoropolymers, and polyamide-imides.

Electrically insulating regions 2, 20 physically separate and electrically insulate electrode 21/210 from other electrodes 41/410, 51/510 of probe 10. The electrically insulating members 2, 20 can have a distal cylindrical portion that is greater in outer diameter and wall thickness than a proximal cylindrical portion. A central lumen passing through the distal and proximal portions of the electrically insulating member can have a substantially uniform diameter that is equal to or greater than the outer diameter of electrode 21. Non-limiting methods of making an electrically insulating piece can include extrusion (including co-extrusion), molding (including co-injection molding), and others known to one skilled in the art.

The proximal and distal portions of the electrodes 21/210, 41/410, 51/510 can have the same or different compositions, and can independently be comprised of one or more electrically conductive materials, including one or more metals and alloys thereof, such as various grades of stainless steel. Electrode 21/210 can have one or more lumens there through and one or more openings positioned at the distal ends of the active electrode 21/210 as well as on the side of portions of the electrode 21/210 for delivery of substances, including, but not limited to, infusion media, solutions or suspensions containing one or more therapeutic agent as well as diagnostic agents, hydrogels, and colloidal suspensions containing nanoparticles as well as microparticles. In certain embodiments the substances can be delivered to increase the conductivity of the tissue and in others are delivered to increase the efficiency of ablation. In other embodiments the substances are released to alter the conductivity of tissue.

Electrically insulating members 2, 20 can be coaxially disposed about at least a portion of at least one voltage delivery member. Electrically insulating members 2, 20 can be coextensive distally with at least a portion of at least one voltage delivery member, and can extend into handle 3. Electrically insulating members 2, 20 can include one or more insulative regions 2, 84 of the same or different electrically non-conductive materials. Electrically insulating members 2, 20 can electrically insulate at least a portion of at least one voltage delivery member to prevent electrical shorting and arcing thereof, which can adversely affect treatment efficiency as well as efficacy. Use of multiple layers as well as coatings to form electrically insulating members 2, 20 can help to reduce or eliminate the occurrence of pin holes or damages therein during the manufacturing process. When assembling probes 1, 10, electrically insulating members 2, 20 can be applied onto the trocar 9, 90 by methods such as, but not limited to, sliding on and shrink-wrapping one or more tubular structures (including sleeves as well as tubing) of thermoplastics, forming one or more surface coatings, such as vapor deposition, spraying, dipping, as well as molding.

Optionally, one or more of electrodes 21/210, 41/410, 51/510 can be rendered more echogenic than other regions, including the electrically insulating regions 2, 20. Certain embodiments include non-limiting methods for echogenicity enhancement including particle blasting, echogenic coating, perforating, chemical etching, and laser etching. In certain embodiments, microabrasive blasting is applied to voltage delivery regions to achieve a depth of 70 microns.

FIG. 5A illustrates one exemplary embodiment of a handle 3 of the probe body. One of ordinary skill in the art will recognize that other configurations can be used. The handle 3 comprises an outer surface, a proximal end 17, a distal end 11 and an interior or cavity 56. The distal portion 11 of the handle can comprise an opening 22 defined therein a distal face 60 of the handle 3 such that it is sized to allow an outer surface of the trocar 9, 90 extend through the opening 22. The opening 22 faces substantially in a distal direction toward the tissue piercing tip 23, 230 of the probe 1. As illustrated in FIG. 5A, in embodiments where the insulative sleeve 45 is non-moveable, the proximal end of the trocar 9, along with the insulative sleeve 45, which coaxially surrounds the outer surface of the trocar 9 will be secured within the handle 3 to a portion of the interior 56 of the handle 3.

As illustrated in FIG. 5A, and described further herein, in one exemplary embodiment, a deployment means such as, but not limited to, a tension wire member 28 can be coupled to at least a portion of the slide member 7 at the proximal end of the device and can extend along the longitudinal axis within the lumen 19 of the trocar 9 to a distal end of the trocar 9, where the tension wire member 28 can be operatively coupled to an anchoring mechanism 8 (shown in FIGS. 6B through 11) that is deployable from the distal end of the trocars 9, 90.

As illustrated in FIG. 5B, in yet another embodiment, the handle 3 can comprise at least one switching means that can be configured to independently selectively activate at least one electrode. In one aspect, the switching means is coupled to at least one of the electrodes 21/210, 41/410, 51/510. The switching means allows a user to switch any of the electrodes or electrodes 21/210, 41/410, 51/510 between an active or "on" mode and an inactive or "off" mode, thereby allowing a user to control the location of each ablation. In one exemplary embodiment, the switching means can comprise at least one wire member 61 that can be configured to make electrical contact with at least one of the one or more electrodes 51/510, 41/410, 21/210 as the slide member 7 is moved along the outer surface of the handle 3. When the wire member 61 is moved or slides across each electrode 51/510, 41/410, 21/210, the wire member 61 can contact at least one of the proximal electrodes 51/510, 41/410, 21/210. As each of the proximal electrodes is activated, the distal portion of each of the corresponding electrodes 21/210, 41/410, 51/510, in turn, is activated or energized as the wire member 61 makes contact with each of the proximal electrodes. Thus, each electrode can be independently activated, while the remaining electrodes remain inactive. When two probes 1, 10 are being used, a wire member 61, 610 (not shown) for probes 1, 10, respectively, that is capable of contacting each of the electrodes 21, 210 can simultaneously activate electrodes 21, 210 when wire members 61, 610 simultaneously make electrical contact with the electrodes 21, 210, thereby allowing the delivery of energy to a target tissue. By switching between the various active energy delivery modes, a user can perform overlapping ablations without adjusting the position of the ablation device. The use of the switching means allows a user to adjust the area of the tissue treated, adjust the rate of tissue treatment, and adjust the amount of energy delivered to the tissue in order to prevent thermal damage to non-target tissue including coagulation of blood vessels such as the hepatic vein. This mechanism also helps to generate a more uniform ablation profile.

Figure 5C:
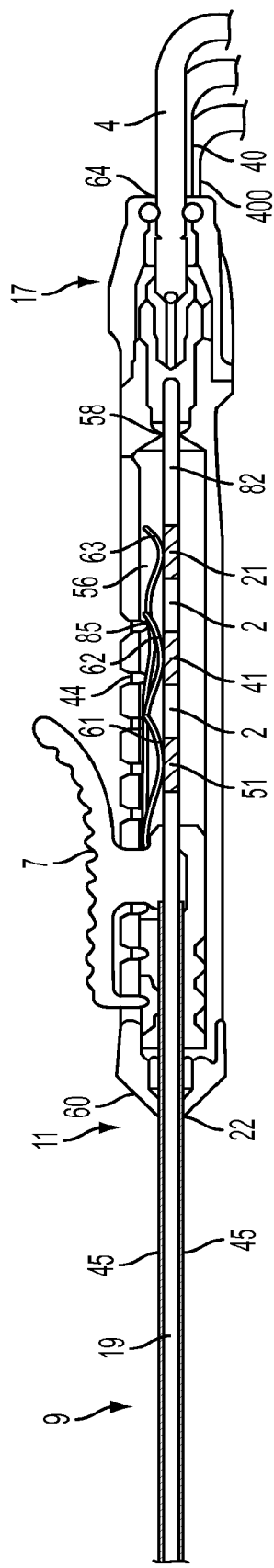
FIG. 5C illustrates an enlarged longitudinal sectional view of another embodiment of the handle of the energy delivery probe.

One of ordinary skill in the art will recognize that various embodiments of the handles illustrated in FIGS. 5A through 5C could be used alone or in combination, depending on the desired features. For example, in one aspect, the handle 3 may comprise at least one tension wire member 28 that can extend the length of the lumen and can be operatively coupled to at least one anchoring means at the distal end of the device, described herein, in addition to at least one wire member 61 that can be operatively coupled to at least one electrode 21, 41, 51.

The trocars 9, 90 can extend proximally into cavity 56 of the handle 3 and can terminate in a distal-facing recess of plug 58. Plug 58 can be fixedly coupled to handle 3 to cap off the interior cavity 56 of the handle 3. As such, a portion of energy delivery probe 1 can be fixedly coupled between at least opening 22 and plug 58 within handle 3. Adhesives or other non-limiting bonding techniques can be used to render probe 1 immovable relative to handle 3. Although opening 22 has a substantially circular shape, one of ordinary skill in the art will recognize that the opening 22 can have other shapes as well, including, but not limited to, elliptical or crescent shaped.

A proximal opening 64 can be defined in the outer surface at the proximal end of the handle 3 such that it is configured for receiving one or more cables 4, 40 from cavity 56. In the embodiments described herein, the ablation device can comprise two cables 4, 40 because at least two probes 1, 10 will be used to ablate tissue. Each of cables 4, 40 can be connected to a probe 1, 10. The one or more cables 4, 40 can be electrically coupled to proximal portion 82 of the trocar 9, thus also to any one of the electrodes 21, 41, 51, through at least one lead wire 35. Non-limiting examples of coupling methods include, but are not limited to, soldering, lead wire wounding, electrically conductor lugs, and combinations thereof.

In one aspect, cavity 56 can be at least partially filled with a flowable material, including but not limited to a liquid, semi-liquid, as well as a gel, and a hardening material, such as, but not limited to at least one of a cross-linkable, polymerizable, or otherwise curable material, that is electrically insulating, such as epoxy, to secure and immobilize the various components within the cavity 56 of the handle 3, as well as provide electrical insulation among the various components and between the components and a device operator. The components within the handle 3, including cables 4, 40, and lead wire 35, in addition to other components, are immobilized relative to handle 3. The handle design is configured to prevent ingression of fluids into handle 3. As illustrated in FIG. 5C, in yet another embodiment, each electrode 21, 41, 51 can be in electrical contact with a separate wire members 61, 62, 63, respectively. Thus, each of the electrodes can be in separate electrical contact with three separate wire members 61, 62, and 63.

FIGS. 6A through 11 illustrate various anchoring mechanisms 8 that are deployable from the distal end of the ablation probe. In one aspect, the anchoring means 8 can incorporate a means for collecting a biopsy sample. As illustrated in FIGS. 6A through 6C, the ablation probe can comprise a stationary insulative sleeve 45. As illustrated in FIG. 6B, the trocar 9, 90 acts as a sleeve from which the anchoring means can be deployed. The anchoring means 8 can be a distally adjustable loop anchoring structure that can help restrain the ablation probe and anchor the ablation probe in place within the tissue after the probe is inserted into the tissue and before an ablation procedure is performed. The distally adjustable loop anchoring means 8 can comprise oppositely disposed arcuate sections that are joined on both ends. In one aspect, the anchoring means 8 can comprise at least a first arcuate portion and a second arcuate portion, which portions are symmetric with respect to each other. In one aspect, the anchoring means 8 can comprise at least one wire 50. In one aspect, the anchoring means 8 can comprise more than one type of wire member 50, which wires can be symmetric with respect to each other. Each of the first arcuate portion and the second arcuate portions can be joined together by soldering, press-fitting, and the like at a distal-most tip in a secure manner and positioned within tip cover 46. Each of the arcuate wire members 50 can have smooth edges so that the anchoring means is non-traumatic to a patient's tissue after it is implanted. In one aspect, the anchoring means 8 can be biased such that it is radially expandable from a collapsed position to an expanded position from the distal tip of the probe 1. In one aspect, the wire members 50 can be comprised of a shape memory material, such as, but not limited to, Ni Ti, or another shape-memory material.

FIGS. 7A through 7C illustrate another embodiment of the anchoring means 8. In this embodiment, the ablation probe 1 can comprise an adjustable sleeve which can comprise an active electrode 21 and an insulative sleeve 45. In one aspect, the active electrode portion 21 is positioned at the distal end of the sleeve, and the insulative portion 45 is positioned proximally of the active electrode portion 21. The sleeve coaxially surrounds insulative region 2. The sleeve enables a user to adjust the positioning of the active electrode 21 portion and to control the retraction and deployment of the anchoring means 8. In this embodiment, the anchoring means 8 can comprise a plurality of wire members 50. A portion of such member 50 can be arcuate in the deployed position. As described above, the anchoring means 8 can be operatively connected to at least one tension control or wire member 28, illustrated in FIG. 5A. The tension control wire member 28 can extend longitudinally along at least one lumen 19 of the trocar 9 and can be proximally pulled by, a user in order to deploy the anchoring means 8 from the distal end of the trocar 9 into the tissue. The tension control wire member 28 can be used for applying an adjustable amount of tension, to force, or to relax, or change the shape of the arcuate sections of the anchoring means 8. In one aspect, the tension control member 28 can be a wire or a tube that can be operatively connected to the slide member 7, as illustrated in FIG. 5A. The anchoring means 8 can be a self-expanding member, or alternatively, the anchoring means can be manually expanded or manipulated by use of the tension wire member 28.

As illustrated in FIGS. 7A and 7B, the anchoring means can comprise two or three wire members that are compressed within a sub-tube that can be retracted into the distal end of the ablation probe. In one aspect, the wire members can be flat or round and may have a blunt tip. The tension control member 28 may be deployed by proximally pulling back the slide member 7, thereby moving the anchoring member 8 distally and deploying the electrodes from the distal edge of the trocar. Once the anchor is exposed, the center tension control wire member 28 can be further tightened or pulled proximally toward the user, causing at least a portion of the plurality of wire members to radially expand outwardly, thereby creating a more expanded anchor member shape.

As described above, the tension control wire member 28 can be positioned within a portion of the handle 3 and can extend through at least one lumen 19 of one of the trocars. The proximal end of the tension member 28 can be operatively coupled to the slide member 7 that is manually slideable thereon the handle 3, and the distal end of the tension member 28 can be operatively coupled to the anchoring member 8. The anchoring member 8 can be deployed from the distal end of the trocar 9 by sliding the actuating/slide member proximally along the trocar. The wires can be deployed after the center tension control wire member 28 is pulled toward the proximal end of the device. When the center wire member 50 is pulled in a proximal direction, the remaining wires expand radially outwardly. When tension is removed from the center tension wire member, the outer wires can return to a relaxed position.

In one aspect, as illustrated in FIG. 7A, in the undeployed state the arcuate wire members 50 of the anchoring means 8 can extend along the longitudinal axis of the ablation device. As illustrated in FIG. 7B, in one aspect, the anchoring means 8 can be deployed by retracting the moveable sleeve 69 while keeping the anchoring means 8 stationary, thereby causing the anchoring means 8 to expand from the distal end of the trocar 9. The moveable sleeve 69 can comprise at least one activatable electrode portion 21 and an insulative sleeve 45 portion. Thus, the anchoring means 8 can be deployable and expandable from the distal end of the trocar 9. The probe can comprise more than one anchoring means 8 that can be deployable from the distal end of the probe 1. The anchoring means 8 can comprise at least three wire members 50. In one aspect, each of the wire members 50 can be positioned such that they each lie in a different plane from each of the other two wire members 50, as illustrated in FIG. 7C, such that the wires form a triangular shape.

Figure 9:
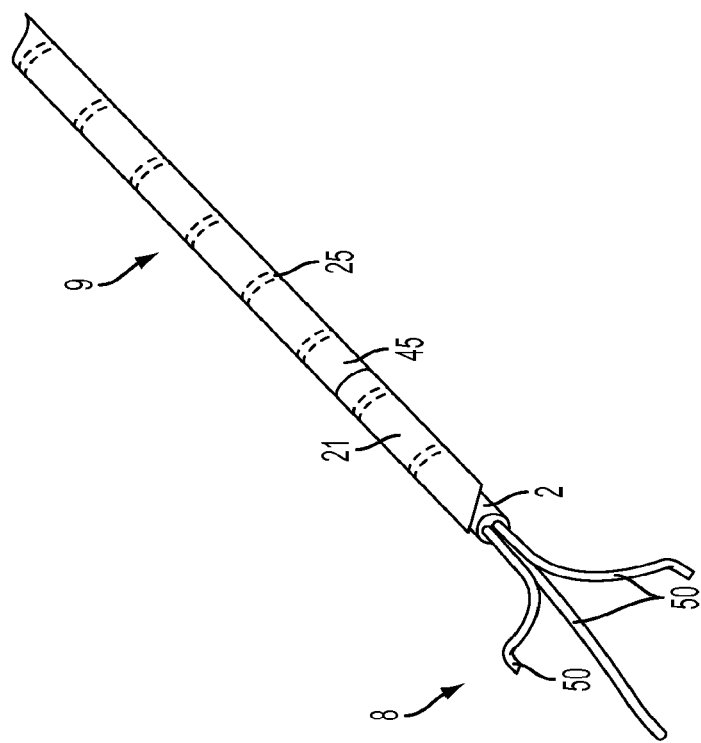
FIG. 9 illustrates an enlarged perspective view of a portion of the distal end of the probe with another embodiment of an anchoring means.
Figure 8:
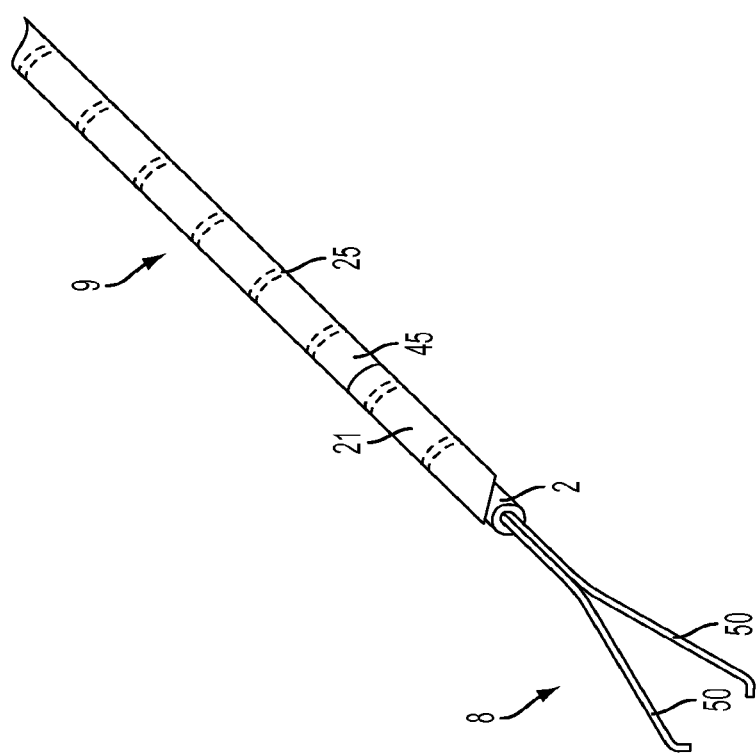
FIG. 8 illustrates an enlarged perspective view of a portion of the distal end of the probe with another embodiment of an anchoring means.

FIGS. 8 and 9 illustrate other embodiments of the anchoring means 8 that can be used with the ablation device described herein. As illustrated in FIG. 8, the anchoring means 8 can comprise two wire members 50 constructed of a flat or round wire or tube, each with a hooked tip. Each of the wire members 50 can be deployed by adjusting the position of the trocar 9 in a proximal direction. Alternatively, the anchoring means 8 can be retracted by sliding the trocar 9 distally over the anchoring means 8. FIG. 9 illustrates yet another embodiment of the anchoring means 8. In this embodiment, the anchoring means 8 comprises three wire members 50. The anchoring means 8 can comprise a single wire member 50 extending longitudinally from the center of the trocar 9, along the longitudinal axis of the trocar and the center wire 50 can be surrounded by at least two laterally extending wire members 50 that can be positioned on either side of the single longitudinally extending wire member 50. Each of the two laterally extending wire members 50 can have a hook formed at the distal tip of each of the laterally extending wire members 50.

Figure 11:
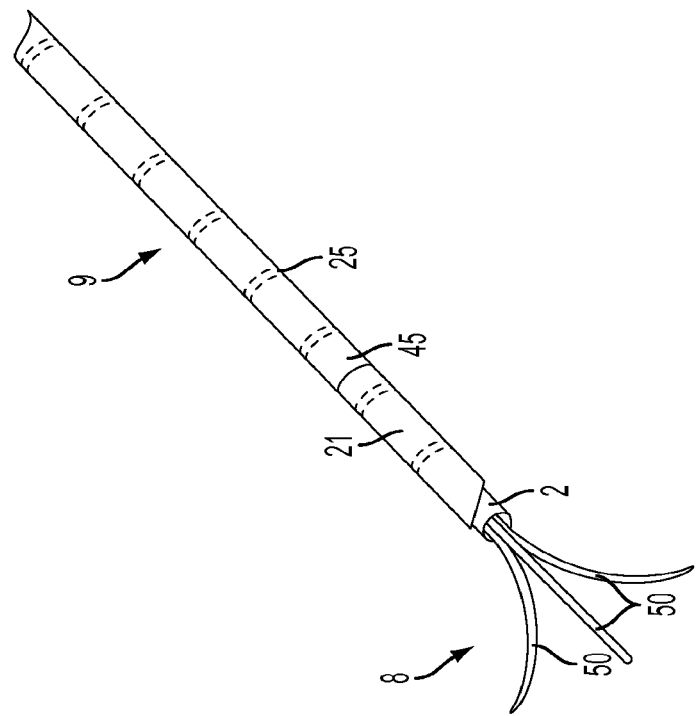
FIG. 11 illustrates an enlarged perspective view of a portion of the distal end of the probe with another embodiment of an anchoring means.
Figure 10:
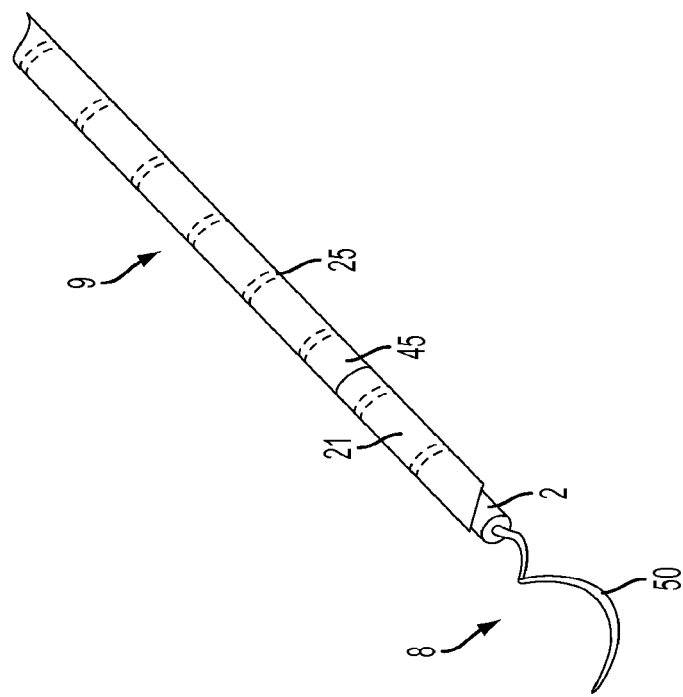
FIG. 10 illustrates an enlarged perspective view of a portion of the distal end of the probe with another embodiment of an anchoring means.

FIGS. 10 and 11 illustrate two additional embodiments of anchoring means 8. In one embodiment FIG. 10 illustrates a single wire member 50. In one aspect, the wire member can have at least a first arcuate section and a second arcuate section that can form an anchor. The first arcuate section can be smaller than the second arcuate section. This anchoring member 8 can be used to anchor the ablation probe in relation to the tissue by rotating the trocar 9. The anchoring means can be removed by rotating and pulling the anchor back into the trocar.

FIG. 11 illustrates another embodiment of the anchoring means 8. In this embodiment, the anchoring means 8 can comprise at least one wire member 50 extending longitudinally from the center of the trocar, and similar to the embodiment in FIG. 10, each wire member 50 can laterally extend away from the longitudinal axis such that the side electrodes are deployed in a laterally outwardly extending direction from the middle longitudinal wire member 50.

Figure 12:
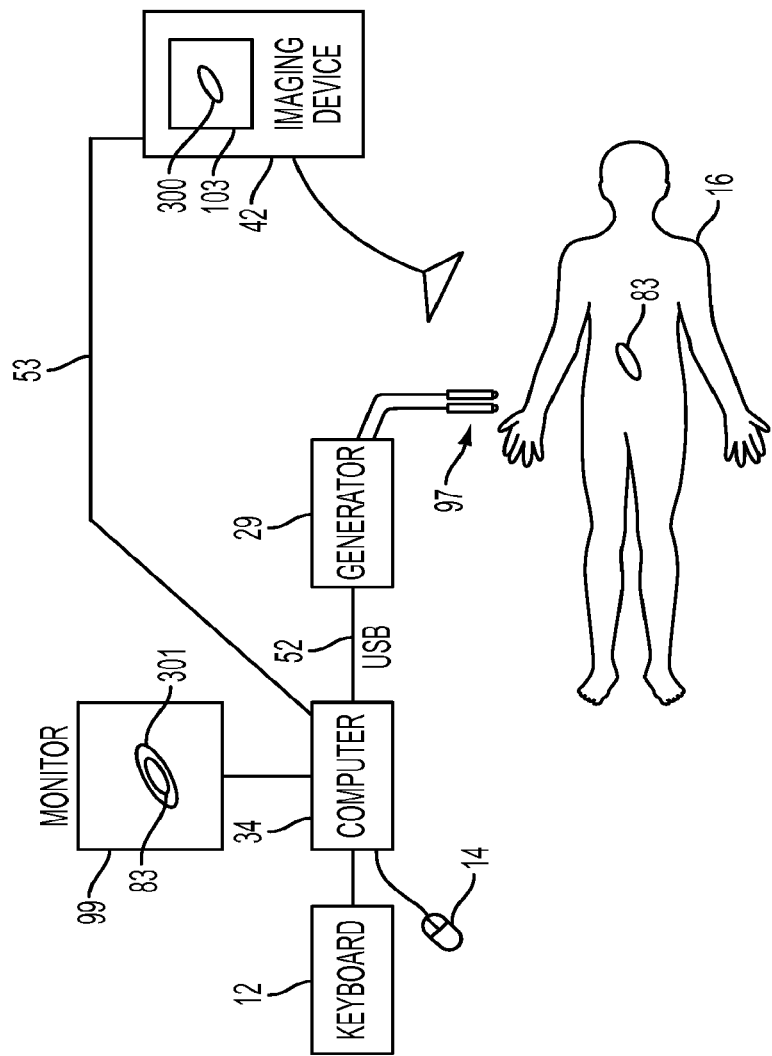
FIG. 12 illustrates a system for use with the energy delivery device described herein.

Referring now to FIGS. 12 through 15C, a method of using the ablation device for IRE or RF ablations to treat a target tissue region is described and illustrated herein. In one aspect, the energy delivery probes 1, 10 described herein can be used with an electrical treatment planning software, such as, but not limited to, that provided by AngioDynamics, Inc. (with the NanoKnife® irreversible electroporation system), described in U.S. patent application Ser. No. 12/751,845, filed Mar. 31, 2010 and Ser. No. 12/751,854, filed Mar. 31, 2010, respectively, which applications are incorporated by reference herein in their entireties. Exemplary components that can be used with the method of the present invention are illustrated in FIG. 12. As described above, one or more probes 1, 10 can deliver therapeutic energy and are powered by a voltage pulse generator, described above, that generates high voltage pulses as therapeutic energy such as pulses capable of irreversibly electroporating the target tissue 83. Although two receptacles 97 for electrodes are illustrated, the voltage pulse generator 29 system can include up to six separate receptacles for receiving up to six individual energy delivery members which can be adapted to be plugged into a respective receptacle. The receptacles can each be labeled with a number in consecutive order. In other embodiments, the voltage pulse generator 29 can have any number of receptacles for receiving more or less than six probes. As described above, each probe 1 can include at least two activatable electrode regions separated by an insulating portion.

The generator or energy source 29 can be connected to a treatment control computer 34 having input devices such as keyboard 12 and a pointing device 14, and an output device such as a display device 99 or monitor for viewing an image of a target treatment area 300 such as a target tissue 83 or target tissue 83 surrounded by a safety margin 301. The computer 34 is attached to a USB 52, which is attached to the generator 29. The computer 34 is also connected to an imaging device 42 via a cable 53. The therapeutic energy delivery device 1 is used to treat a target tissue 83 inside a patient 16. An imaging device 42 includes a monitor 103 for viewing the target tissue 83 inside the patient 16 in real time. Examples of imaging devices 42 include ultrasonic, CT, MRI and fluoroscopic devices as are known in the art. The treatment system can also include computer software, such as treatment control module (not shown), which assists a user to plan for, execute, and review the results of a medical treatment procedure. The treatment control module can display the anticipated ablation zone(s) based on the position of the probes and the treatment parameters and whether the treatment was successful.

The energy delivery probe device 1 can be configured such that the probe 1 can be placed within or adjacent to the target tissue 83, enabling safe usage in situations where the tissue targeted for ablation is adjacent to critical as well as vital non-targeted structures, such as, but not limited to, the urethra or neurovascular bundles. Thus, the disclosed pulsed electric field ablation, when carried out under certain parameters and operating conditions, can selectively spare, including without damaging, destroying or denaturing, certain tissues and structures present within the ablation volume. Non-limiting tissues that can be selectably spared by the pulsed electric field ablation include nervous, vascular, duct, as well as collagen-rich tissues.

Therapeutic energy delivery devices disclosed herein can be designed for tissue destruction in general, such as resection, excision, coagulation, disruption, denaturation, and ablation, and are applicable in a variety of surgical procedures, including but not limited to open surgeries, minimally invasive surgeries (e.g., laparoscopic surgeries, endoscopic surgeries, surgeries through natural body orifices), thermal ablation surgeries, non-thermal surgeries, such as, but not limited to irreversible electroporation (IRE) and radiofrequency (RF), as well as other procedures known to one of ordinary skill in the art.

Figure 13:
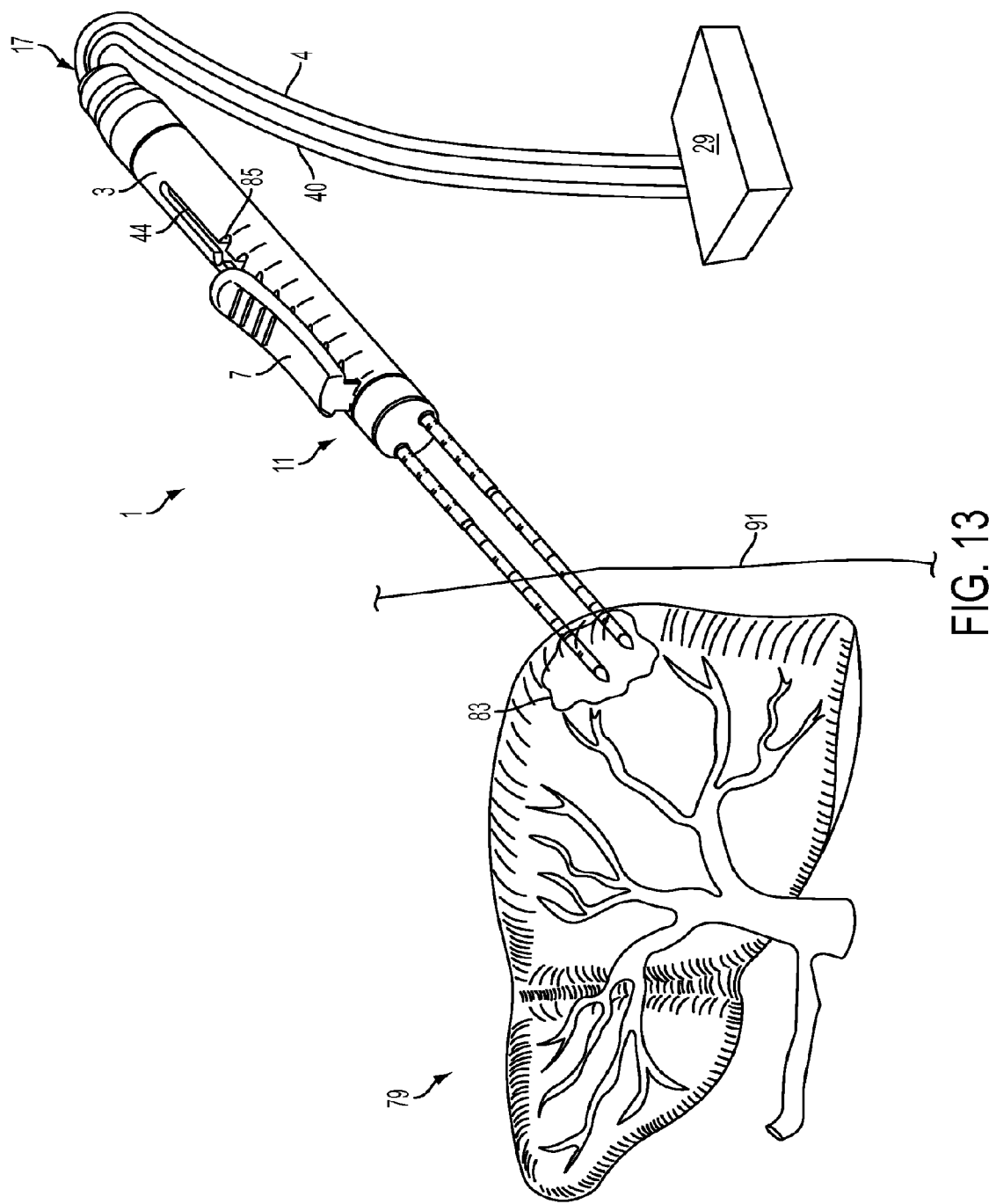
FIG. 13 illustrates a method of using the energy delivery probe described herein to ablate a target tissue.

The method described herein involves identifying a target tissue 83 in a patient 16, as illustrated in FIG. 13. Liver tissue 79 is illustrated in FIG. 13. However, non-limiting examples of tissue masses to which the devices of the present application are applicable include benign tissue masses such as benign prostate hyperplasia (BPH) and uterine fibroids, as well as benign or malignant masses such as cancers and tumors of various tissue types, including, but not limited to, prostate, uterine, lung, liver, kidney, brain, head/neck, bone, stomach, colon, breast, spleen, uterus, vascular, adipose, lymph, ovarian, eye, ear, bladder, skin, and pancreas, or any other desired mammalian target tissue area of a patient's body. The energy delivery probe 1 can be suitable for treatment of conditions for various tissues, volumes, sizes and locations, including small to medium sized tissue volumes, and tissue volumes that are in close proximity to other non-targeted structures, such as, but not limited to, neuronal structures, vascular structures, duct structures, and collagen-rich structures.

An incision in a patient's skin can be created, and one or more probes 1, 10 can be inserted into or near a target tissue 83. The insertion of the one or more probes 1, 10 can be percutaneous, laparoscopic, endoscopic, as well as through natural orifices, including insertions related to orifice translumenal endoscopic surgery. An ablation device can be provided, such as that described above, having at least a first trocar 9 and a second trocar 90 that are spaced in a parallel position relative to each other. In one exemplary aspect, the method can further comprise positioning the first trocar 9 on the first side of the target tissue and the second trocar 90 on the second side of the target tissue. The first and second trocars 9, 90 are inserted into the target tissue 83 such that the first trocar 9 and the second trocar 90 remain substantially parallel during insertion, treatment, and withdrawal of the probe 1, as illustrated in FIG. 13. If using two separate probes, as illustrated in FIG. 2, to help ensure that the trocars 9, 90 remain substantially parallel to each other during insertion and removal, a spacer 59 can be used, as described herein. The electrodes on the first trocar can be substantially parallel to each of the electrodes on the second trocar. Alternatively, at least one of the electrodes on the first trocar can be staggered in position compared to at least one of the electrodes on the second trocar.

Figure 14A:
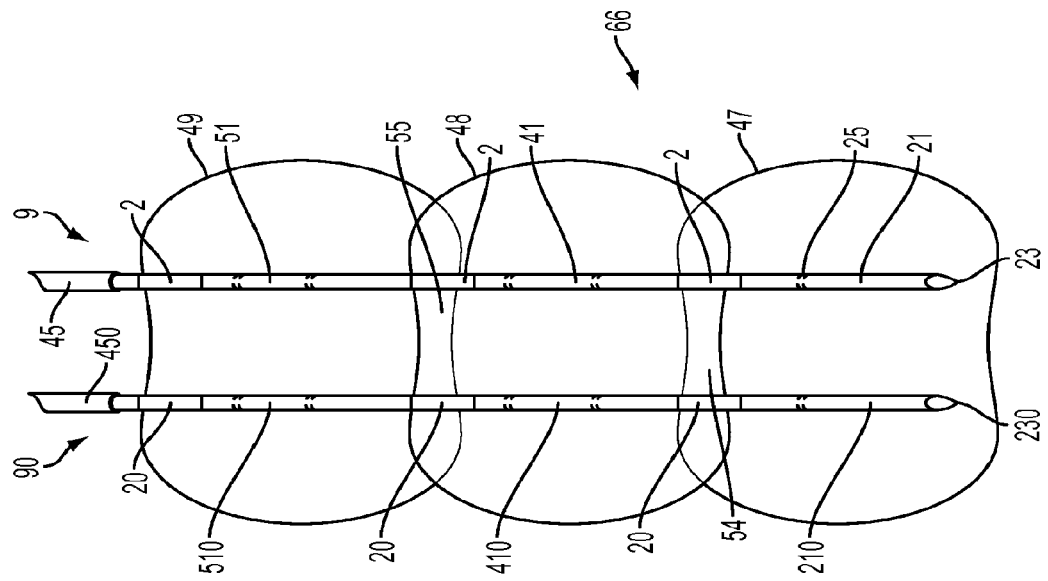
FIG. 14A illustrates exemplary overlapping first and second ablation zones that are produced after first and second ablations are completed.

The method described herein further involves delivering energy from an energy source 29 through any desired combination of at least two activatable electrodes 21/210; 41/410; and 51/510 of the trocars 9, 90 to a target tissue 83 in order to ablate the target tissue, thereby forming a first ablation zone 47, as illustrated in FIG. 14A. In another aspect, the chosen electrode pairs can be combined in any other combination, such as, but not limited to, 21/410, 210/41, and the like, to produce various ablation sizes. In one aspect, the energy can be independently delivered to each electrode. Alternatively, in another aspect, energy can simultaneously or sequentially be delivered to any combination of electrodes 21/210, 41/410, and 51/510. In one aspect, the ablation zone 47 can be about 1 cm in depth and about 3 cm in width. The ablation zone 47 can be defined as the radiologically identifiable region in which an ablation effect was directly induced. In one aspect, the active electrodes 21/210 can be substantially completely surrounded by the resulting ablation zone 47. In any of the methods described herein, the energy delivered to the target tissue 83 can be radiofrequency energy. Alternatively, the energy delivered can be electrical energy in the form of electrical pulses that can be sufficient to cause non-thermal irreversible electroporation of the target tissue 83 but insufficient to cause thermal damage to the target tissue 83 or tissue surrounding the target tissue.

Figure 14B:
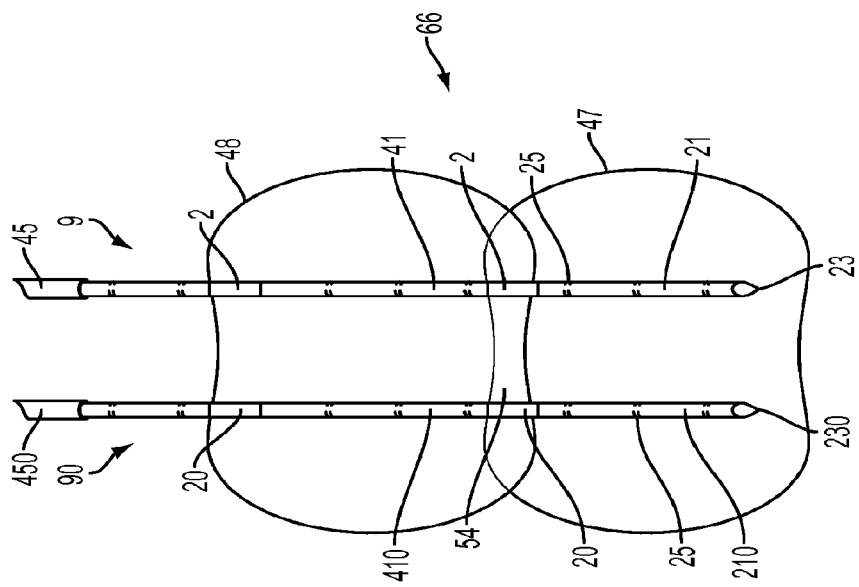
FIG. 14B illustrates exemplary overlapping first, second, and third ablation zones that are produced after first, second, and third ablations are completed.

After a first ablation is completed and a first ablation zone 47 is produced, described above, the method can further involve independently or simultaneously activating a second set of electrodes 41/410 that are positioned on the trocars 9, 90 by delivering electrical energy to the electrodes 41/410 to produce a second ablation zone 48 that can be about 1 cm in depth and about 3 cm in width. As illustrated in FIGS. 14A and 14B, in one aspect, the second ablation zone can be substantially the same size as the first ablation zone 47. Alternatively, the ablation zone size can be altered by changing the amount of energy delivered to the electrodes or by adjusting the energy delivery surface area of the electrodes by other means, such as by adjusting the position of an insulative sleeve 45, as described below. The first ablation one 47 and the second ablation zone 48 form a first overlapping ablation zone 54 that can be substantially concentrated in depth and width around the insulative regions 2, 20. In one exemplary aspect, the overlapping ablation zone 54 can be about 1 cm in depth and about 3 cm in width. After the second ablation procedure, energy can be delivered to a third set of electrodes 51, 510 to create a third ablation zone 49. In one aspect, the third ablation zone 49 can overlap with the second ablation zone 48, thereby forming a second overlapping ablation zone 55. The sum of the ablation zones 47, 48 produces a total ablation zone 66. The ablation procedure can be repeated as many times as necessary with any set of electrodes along the longitudinal length of the trocars 9, 90 in order to produce a final ablation zone 66. The resulting shapes of the ablation zones described and depicted herein are merely exemplary. One of ordinary skill in the art will recognize that many other types and sizes of ablation zones could be produced.

The method of use of any of the probe assemblies described herein presents a substantial advantage over conventional IRE and RF ablation methods. This probe design and method is advantageous because it allows for overlapping ablations without requiring the removal and reinsertion of the ablation probe(s) or the need for pull-back of the probe(s) between ablations before re-treatment when a lesion is larger than the current a particular needle device can treat, thereby avoiding trauma to the patient and decreasing the chance of mis-positioning of the probe. Thus, this ablation device can incorporate several separate treatment sections along the length of the trocar 9, 90. This ablation procedure can be repeated multiple times in various positions along the trocars 9, 90 to achieve a desired ablation zone(s). This method is also beneficial because by eliminating the need to adjust the position of the device, the chance of re-seeding a tumor track is also decreased.

In embodiments that comprise a moveable insulative sleeve 45, such as illustrated in FIGS. 2 and 3, after energy is delivered to the first set of electrodes 21, 210, then one or both of the insulative sleeves 45, 450 can be adjusted along the length of the trocars 9, 90 to a desired position in order to expose one or more additional sets of electrodes. In one exemplary embodiment, before each ablation procedure, the insulative sleeve 45 can be advanced or retracted along the longitudinal length of the trocar 9, 90 to reveal either a partial energy delivery surface of each electrode of a set of electrodes or a complete energy delivery surface of each electrode of a set of electrodes. For example, after energy is delivered to a first set of electrodes 21, 210 to produce a first ablation zone 47, the insulative sleeve 45 can be adjusted, and energy can then be delivered to a second set of electrodes 41, 410, thereby creating a second ablation zone 48. The insulative sleeve 45 can be adjusted again by proximally moving the insulative sleeve 45 to reveal at least a portion of the third set of electrodes 51, 510. Electrical energy can then be delivered to each electrode of the third set of electrodes, thereby creating a third ablation zone 49, which can overlap with the second ablation zone 48 to form an overlapping ablation zone 55. In one aspect, the overlapping ablation zone 55 can be substantially the same size as the overlapping ablation zone 54. In one aspect, the sum of the different ablation zones 47, 48, 49 can produce a total ablation zone 66. In one aspect, any variety of different positions may be utilized to create different ablation geometries for selected tissue masses of different geometric and sizes.

During the methods described above, energy can be applied from the energy source or generator 29 to the electrodes or any of the sets of electrodes in various patterns. Particularly, electrical pulses of various voltages can be applied to the electrode sets described above to the target tissue 83. In one aspect, energy can be applied between a first set of electrodes 21, 210. In another aspect, energy can be successively applied between a second set of electrodes 41, 410. Finally, energy can be successively delivered between a third set of electrodes 41, 410. Each of these ablations produces a similarly size ablation zone. Additional ablations can be performed between any two corresponding electrode pairs of trocars 9, 90. Software can be used to predict ablation zones using various probe configurations. For example, outlining a predicted ablation zone can, be obtained using the finite element method ("FEM") COMSOL Multiphysics Modeling and Simulation, software (Palo Alto, Calif.).

In one exemplary embodiment, 90 electric pulses of a 70 microseconds (μsec) pulse length can be delivered per pair of electrodes 21/210, 41/410, and 51/510 at a voltage gradient of 1250 V/cm to the target tissue. Other suitable pulse parameters may be used such as, but not limited to, between 50 and 100 of between 50 and 100 microseconds (μsec) pulse length at a voltage gradient of between about 500 V/cm and about 3000 V/cm. In one aspect, the pulse parameters can be 70 pulses (7 sets of 10 pulses each) at 100 microseconds, with delays of 3.5 seconds between each set of 10 pulses. Voltage gradient (electric field) is a function of the distance between electrodes and electrode geometry, which will vary depending on the size of the tissue sample, tissue properties, and other factors. The parameters such as amplitude of voltage pulses, duration of each pulse, total number of voltage pulses, and duration between consecutive pulses can be altered, depending on the desired ablation.

As illustrated in FIGS. 15A through 15C, the ablation methods described herein can further involve deploying an anchoring mechanism 8 from the distal end(s) of the ablation probes 1, 10 before or after ablation of a target tissue 83. In one aspect, the anchoring means 8 can be fully retracted within a lumen 19 of the ablation probe trocar before and during insertion of the probes 1, 10 into tissue. After the trocars 9, 90 are inserted into a target tissue 83, the anchoring means 8 can be deployed from the distal end of each of the probes 1, 10 into the tissue to secure the probes 1, 10 in relation to the target tissue 83.

Although one type of anchoring means 8 is illustrated in FIGS. 15A through 15C, any suitable type of anchoring means, such as those means illustrated in FIGS. 6B through 11 can be deployed into the target tissue 83. Depending upon the type of anchoring means used, the method may involve further adjusting a tension wire member 28 to further deploy and/or adjust the position of the anchoring means 8. As described herein, the tension wire member 28 may be pulled proximally to deploy wire members of an, anchoring means 8. In one exemplary aspect, the anchoring means 8 can be deployed within the tissue such that after the ablation zone(s) are produced, the anchoring means 8 are completely surrounded by the ablation zone(s). After the ablation procedure is completed, the method can further involve retracting the anchoring means 8 into the lumen 19 of the trocar 9 and removing the ablation probes 1, 10 from the target tissue. The advantage of deploying the anchoring means 8 in the tissue is that it helps to restrain the active electrode or voltage delivery portion of the trocar throughout an IRE or RF procedure. Deploying the anchoring means 8 before an ablation procedure also helps to secure the distal ends of the probes 1, 10 within the tissue and helps to prevent probe migration, particularly axial probe migration, within the tissue. This helps to ensure accurate and predictable ablation zones.

The above disclosure is intended to be illustrative and, not exhaustive. This description will suggest many variations and alternatives to one of ordinary skill in this art. All these alternatives and variations are intended to be included within the scope of the claims where the term "comprising" means "including, but not limited to". The words "including" and "having," as used herein including the claims, shall have the same meaning as the word "comprising." Those familiar with the art can recognize other equivalents to the specific embodiments described herein, which equivalents are also intended to be encompassed by the claims.

Therapeutic energy delivery devices disclosed herein are designed for tissue destruction in general, such as resection, excision, coagulation, disruption, denaturation, and ablation, and are applicable in a variety of surgical procedures, including, but not limited to, open surgeries, minimally invasive surgeries (e.g., laparoscopic surgeries, endoscopic surgeries, surgeries through natural body orifices), thermal ablation surgeries, non-thermal surgeries, as well as other procedures known to one of ordinary skill in the art. The devices may be designed as disposables or for repeated uses.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent possessing claim other than the specific claim listed in such dependent claim below.

Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions can be provided by alternative embodiments without departing from the scope of the appended claims. In this regard, for example, different combinations of elements and/or functions than those explicitly described above are also contemplated as can be set forth in some of the appended claims.

This completes the description of the selected embodiments of the invention. Those skilled in the art can recognize other equivalents to the specific embodiments described herein which equivalents are intended to be encompassed by the claims attached hereto.

What is claimed is:

1. A method of treating a patient, wherein the method comprises:
   identifying a target tissue;
   providing at least one energy delivery probe comprising
      at least a first shaft and a second shaft, wherein each shaft comprises at least a first electrode and a second electrode that are electrically insulated from each other, and wherein each electrode is independently selectively activatable, and
      an insulative sleeve positioned in a coaxially surrounding relationship to at least a portion of each of the first shaft and the second shaft,
   inserting the probe into or near the target tissue; and
   delivering electrical energy between the first electrode on the first shaft and the first electrode on the second shaft to ablate the target tissue, thereby forming a first ablation zone, the first electrodes of the first and second shafts defining a first combination of electrodes;
   switching to a second combination of electrodes such that at least one electrode in the second combination is different from the first combination without repositioning the probe;
   delivering energy to the switched second combination of electrodes to ablate the target tissue, thereby forming a second ablation zone.

2. The method of claim 1, wherein the method further comprises simultaneously delivering energy to the first electrode on the first shaft and the first electrode on the second shaft.

3. The method of claim 1, wherein the method further comprises inserting the probe into or near the target tissue such that the shafts are substantially parallel, and at least one of the electrodes on the first shaft is substantially parallel to at least one of the electrodes on the second shaft.

4. The method of claim 1, wherein the first ablation zone and the second ablation zone are overlapping.

5. The method of claim 1, wherein the method further comprises: before delivering energy to the first combination of electrodes, adjusting the position of at least one of the insulative sleeves.

6. The method of claim 1, wherein the method further comprises: after delivering energy to the first combination of electrodes, adjusting the position of at least one of the insulative sleeves.

7. The method of claim 1, wherein the method further comprises delivering energy selected from the group comprising: electrical energy, radiofrequency (RF) energy, and microwave energy.

8. The method of claim 7, wherein the method further comprises delivering electrical energy to the tissue sufficient to cause irreversible electroporation of the target tissue but insufficient to cause thermal damage to the target tissue.

9. The method of claim 7, wherein the probe further comprises a proximal end, a distal end, and at least one anchor positioned at the distal end of the probe, and wherein after inserting the probe into the target tissue, the anchor is deployed to securely position the probe in relation to the target tissue.

10. A method of treating a patient, wherein the method comprises:
    identifying a target tissue;
    providing at least one energy delivery probe comprising
    at least a first shaft and a second shaft, wherein each shaft comprises at least a first electrode and a second electrode that are electrically insulated from each other, and wherein each electrode is independently selectively activatable, and
       an insulative sleeve positioned in a coaxially surrounding relationship to at least a portion of each of the first shaft and the second shaft,
    inserting the probe into or near the target tissue;
    infusing a fluid through the probe, wherein the fluid is delivered to the target tissue;
    delivering electrical energy simultaneously between the first electrode on the first shaft and the first electrode on the second shaft to ablate the target tissue, thereby forming a first ablation zone, the first electrodes of the first and second shafts defining a first combination of electrodes;
    switching to a second combination of electrodes such that at least one electrode in the second combination is different from the first combination without repositioning the probe;
    delivering energy to the switched second combination of electrodes to ablate the target tissue, thereby forming a second ablation zone.

11. The method of claim 10, wherein the step of delivering electrical energy simultaneously between the first combination of electrodes to ablate the target tissue, thereby forming a first ablation zone is sufficient to irreversibly electroporate the target tissue.

* * * * *